(12) United States Patent
Yokosawa et al.

(10) Patent No.: US 10,292,616 B2
(45) Date of Patent: May 21, 2019

(54) MAGNETIC RESONANCE IMAGING DEVICE

(71) Applicant: HITACHI, LTD., Chiyoda-ku, Tokyo (JP)

(72) Inventors: Suguru Yokosawa, Tokyo (JP); Hisaaki Ochi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 234 days.

(21) Appl. No.: 15/504,684

(22) PCT Filed: Aug. 27, 2015

(86) PCT No.: PCT/JP2015/074222
§ 371 (c)(1),
(2) Date: Feb. 17, 2017

(87) PCT Pub. No.: WO2016/043010
PCT Pub. Date: Mar. 24, 2016

(65) Prior Publication Data
US 2017/0281041 A1 Oct. 5, 2017

(30) Foreign Application Priority Data
Sep. 17, 2014 (JP) .................. 2014-189392

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/7207* (2013.01); *G01R 33/56341* (2013.01);
(Continued)

(58) Field of Classification Search
CPC ................ A61B 5/055; A61B 5/7207; G01R 33/56341; G01R 33/56509; G06T 7/246
See application file for complete search history.

(56) References Cited

U.S. PATENT DOCUMENTS 6,853,189 B1* 2/2005 Pipe ................. G01R 33/56341
324/307
8,395,386 B2 3/2013 Kimura et al.
(Continued)

FOREIGN PATENT DOCUMENTS

JP  2001-292976 A  10/2001
JP  2011-062508 A  3/2011

OTHER PUBLICATIONS

Alhamud A. et al., "Volumetric navigators for real-time motion correction in diffusion tensor imaging", Magnetic Resonance in Medicine, 2012, 68, pp. 1097-1108.
(Continued)

*Primary Examiner* — Dixomara Vargas
(74) *Attorney, Agent, or Firm* — Mattingly & Malur, PC

(57) ABSTRACT

There is provided a technique for DWI measurement, in which MPG application is performed in many directions, that enables detection of presence or absence of body motion during imaging without prolongation of imaging time. A plurality of image groups each comprising 6 or more diffusion-weighted images selected from a plurality of diffusion-weighted images are created so the groups differ from one anther in one or more diffusion-weighted images included in each of the groups. Value of a predetermined diffusion index representing a characteristic amount of diffusion-weighted image is calculated for each image group from the diffusion-weighted images included in each image group. Value of a predetermined body motion index relating to body motion information is calculated from the value of the diffusion index for each image group. Presence or absence of body motion is determined for each image group on the basis of the value of the body motion index.

10 Claims, 16 Drawing Sheets

(51) Int. Cl.
*G01R 33/563* (2006.01)
*G01R 33/565* (2006.01)
*G06T 7/246* (2017.01)
*G01R 33/561* (2006.01)

(52) U.S. Cl.
CPC ........ *G01R 33/56509* (2013.01); *G06T 7/246* (2017.01); *A61B 2576/00* (2013.01); *G01R 33/5616* (2013.01); *G06T 2207/10016* (2013.01); *G06T 2207/10092* (2013.01)

(56) References Cited

U.S. PATENT DOCUMENTS

| | | | |
|---|---|---|---|
| 9,916,648 B1 * | 3/2018 | Tseng | G01R 33/5608 |
| 2011/0043206 A1 | 2/2011 | Kimura et al. | |
| 2012/0259199 A1 | 10/2012 | Huwer et al. | |

OTHER PUBLICATIONS

Aksoy M., et al., "Real-time optical motion correction for diffusion tensor imaging", Magnetic Resonance in Medicine, 2011, 66, pp. 366-378.
International Search Report of PCT/JP2015/074222 dated Nov. 17, 2015.
International Preliminary Report on Patentability received in corresponding International Application No. PCT/JP2015/074222 dated Mar. 30, 2017.

* cited by examiner

Fig. 5
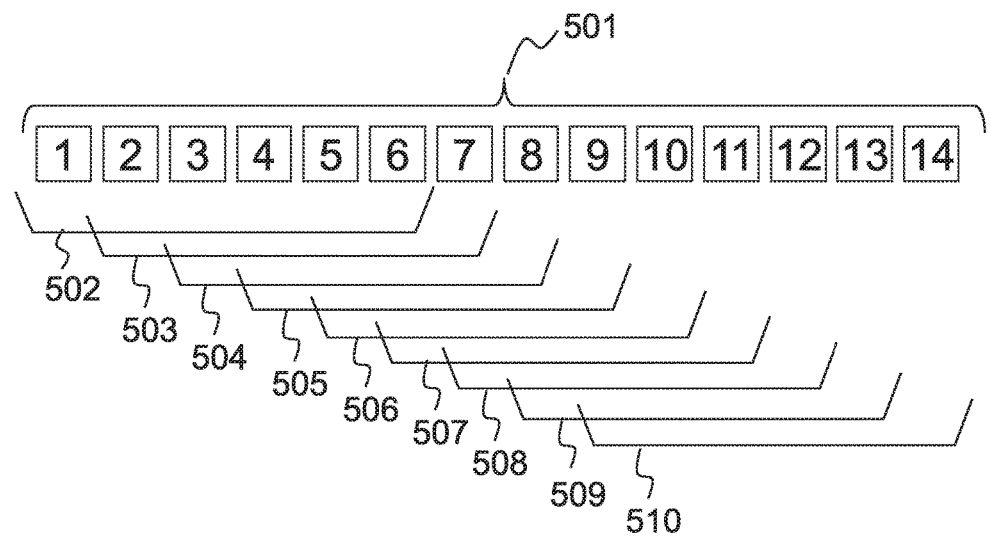
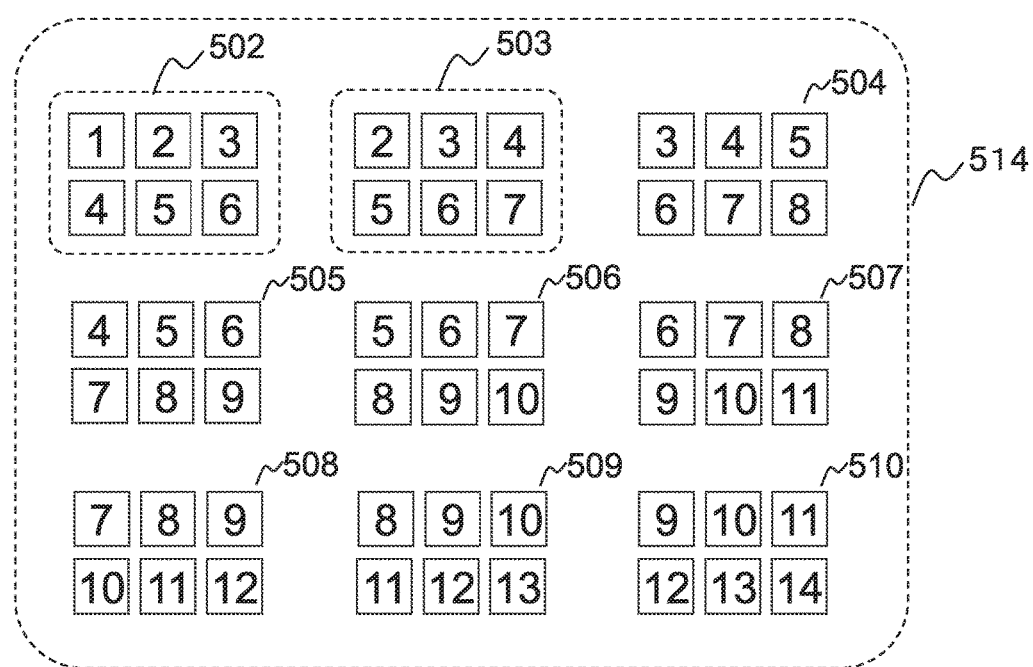

MAGNETIC RESONANCE IMAGING DEVICE

TECHNICAL FIELD

The present invention relates to techniques for measurement of a diffusion-weighted image using a magnetic resonance imaging apparatus and image processing.

BACKGROUND ART

Magnetic resonance imaging (henceforth abbreviated as MRI) apparatuses are diagnostic imaging apparatuses for medical use, which utilize nuclear magnetic resonance phenomenon of, mainly, protons. MRI apparatuses enable non-invasive imaging of an arbitrary section, and enable acquisition of morphological information and information on biological functions such as blood flow and metabolic functions. In general, on a test subject placed in a static magnetic field, a slice gradient magnetic field and a radio frequency magnetic field of a specific frequency are simultaneously applied to excite nuclear magnetization in a section desired to be imaged. A phase encoding gradient magnetic field and a read-out gradient magnetic field are applied on the excited nuclear magnetization to impart two-dimensional positional information, and magnetic resonance signals (echoes) generated by the nuclear magnetization are measured. The measurement of the magnetic resonance signals is repeated until the measurement space called k-space is filled. The signals filled in the k-space are subjected to inverse Fourier transform, and thereby converted into an image.

Pulses for generating echoes and gradient magnetic fields are applied according to a pulse sequence set beforehand. As this pulse sequence, various pulse sequences for various purposes are known.

One of the important diagnostic images obtainable by MRI is diffusion-weighted image (DWI). DWI is an image in which self-diffusion of water molecules contained in a biological tissue is emphasized. A lesion of cerebral infarction at an acute stage immediately after onset can be imaged as DWI, and it is known that it shows contrast different from those of T1-weighted image and T2-weighted image. DWI is obtained by applying MPG (motion probing gradient), which induces reduction of signal intensity by dephasing, on nuclear spins in random motions of a subject, and then measuring echoes to obtain signals corresponding to diffusion rate of the nuclear spin. Since the reduction of signal intensity due to dephasing is caused by nuclear spin diffusing in the direction of the application of MPG, diffusion information for an arbitrary direction can be obtained by controlling the application direction of MPG. Further, diffusion weighting degree can be adjusted by varying the diffusion factor (b value), which is a parameter relating to application intensity and time of MPG, and an image of a higher diffusion weighting degree can be obtained with a higher b value.

As a technique for measuring spatial diffusion distribution of water molecules, there is DTI (diffusion tensor imaging). DTI is based on assumption of a normally distributed three-dimensional elliptic diffusion model, and is widely used as a technique for analyzing degeneration of tissues or structure of nerve tract of white matter by calculating mean diffusivity (MD), and diffusion fractional anisotropy (FA). The pulse sequence for DTI is constituted so that pulse sequence of DWI is repeated with changing the application direction of MPG. Since this pulse sequence requires calculation of components of diffusion tensor, the measurement is performed by successively applying MPG for 6 or more non-parallel independent directions.

Diffusion kurtosis imaging (DKI), which is based on assumption of a non-normally distributed diffusion model, has also been proposed in recent years as a technique for emphasizing degree of diffusion movement restriction caused by cell membranes, intracellular organelles, and so forth. This technique is expected as a technique for capturing change of microstructures accompanying tissue degeneration or cell proliferation in contrast to DTI in which a normally distributed diffusion model is assumed. The pulse sequence of DKI is constituted so that the pulse sequence of DTI is repeated with changing the b value. Since components of the diffusion tensor and kurtosis tensor are calculated in this technique, it is necessary to perform the measurement by applying MPG in 15 or more non-parallel independent directions with three or more of different b values.

In the measurement of DTI and DKI, body motion of a patient under imaging generally causes a computational error in an image reconstructed after the measurement, for example, computational errors of MD (mean diffusivity) and FA (diffusion fractional anisotropy). Although an image not influenced by body motion is desired, it may be difficult to distinguish computational error caused by body motion from signal change caused by pathological change, and it is difficult to determine presence or absence of body motion during imaging only from a calculated image. Further, in DWI, contrast of image changes with change of the application direction of MPG, and therefore it is difficult to detect presence or absence of body motion and correct it only from simple comparison of DWIs obtained with different MPG application directions.

Concerning this problem, for example, Non-patent document 1 proposes a method for performing correction for body motion in DTI by adding pulses for measuring data for the correction for body motion to the pulse sequence of DWI. Non-patent document 2 proposes a method of detecting body motion of a patient under imaging with an optical camera attached to a receiver coil and correcting it by using a checkerboard attached to the patient, which serves as a target.

Patent document 1 discloses a technique for detecting changes of position and direction of a patient (body motion) by obtaining three diffusion-weighted images as one group with three MPG application directions perpendicular to one another, obtaining a mean diffusivity image (trace-weighted MR result image) from the three diffusion-weighted images by calculation, and comparing it with a previously obtained mean diffusivity image. In this technique, while diffusion-weighted images are obtained for a plurality of groups of different combinations of the three application directions of MPG, mean diffusivity images are calculated, and body motion is temporally detected. It also discloses correction of diffusion-weighted images according to detected body motion (position and direction).

PRIOR ART REFERENCES

Patent Document

Patent document 1: U.S. Patent Published Application No. 2012/0259199

Non-Patent Documents

Non-patent document 1: Alhamud A, Tisdall M D, Hess A T, Hasan K M, Meintjes E M, van der Kouwe A J, "Volumetric navigators for real-time motion correction in diffusion tensor imaging", Magnetic Resonance in Medicine, 2012, 68, pp. 1097-1108

Non-patent document 2: Aksoy M, Forman C, Straka M, Skare S, Holdsworth S, Hornegger J, Bammer R, "Real-time optical motion correction for diffusion tensor imaging", Magnetic Resonance in Medicine, 2011, 66, pp. 366-378

SUMMARY OF THE INVENTION

Object to be Achieved by the Invention

The technique described in Non-patent document 1 suffers from a problem that the imaging time is prolonged by the additional measurement for body motion correction.

Since the technique described in Non-patent document 2 does not require additional measurement, imaging time is not extended, but time and effort for attaching the target to the subject are required. Further, when the subject has traumatic injury, there is assumed a case where it is difficult to attach the target to the subject depending on degree of the injury. Furthermore, since restriction is imposed on the positional relationship of the target and the optical camera, receiver coil usable for the imaging is limited. It also suffers from a problem of increase of cost, since it requires installation of an external monitor system.

In the technique described in Patent document 1, the MPG application directions of the three diffusion-weighted images for obtaining a mean diffusivity image must be perpendicular to one another. If there is used a method of obtaining one mean diffusivity image by obtaining three diffusion-weighted images with predetermined three directions perpendicular to one another, and then obtaining one mean diffusivity image by obtaining three diffusion-weighted images with three directions perpendicular to one another and shifted from the foregoing three directions perpendicular to one another, the MPG application directions are kept uniform to a certain extent over the whole process, but temporal resolution of the detection of body motion is limited to a frequency of once per acquisition of three diffusion-weighted images. On the other hand, if it is attempted to obtain three diffusion-weighted images with three MPG application directions perpendicular to one another as a combination of one diffusion-weighted image and two immediately preceding diffusion-weighted images at the time of every imaging of one diffusion-weighted image in order to increase temporal resolution of body motion detection with such three directions perpendicular to one another as described in Patent document 1, the MPG application directions usable in the whole process are limited to the three directions, and DTI that requires measurement along six axes of different directions cannot be used. If a mean diffusivity image is created by combining one diffusion-weighted image with two immediately preceding diffusion-weighted images at the time of every imaging of one diffusion-weighted image with neglecting the relation of three directions perpendicular to one another, the mean diffusivity should contain errors, and therefore precision of body motion detection is decreased.

Further, in the technique described in Patent document 1, body motion is detected by comparing a newly obtained mean diffusivity image with a previously obtained mean diffusivity image as a reference, and therefore if the reference image contains body motion, it cannot be corrected. Furthermore, in the technique of Patent document 1, position and direction in a diffusion-weighted image are corrected according to body motion, but errors in an image generated by deviation of the MPG application direction from the correct application direction caused by body motion are not corrected. Therefore, characteristic amounts of the mean diffusivity, diffusion fractional anisotropy, and so forth include errors.

The present invention was accomplished in view of the aforementioned problems, and an object of the present invention is to provide a technique for DWI measurement, in which MPG is applied in many directions, that can detect presence or absence of body motion under imaging without prolonging imaging time.

Means for Achieving the Object

The present invention provides an MRI apparatus comprising a measurement part that acquires a plurality of diffusion-weighted images by applying diffusion gradient magnetic field pulses for a plurality of predetermined different directions according to a predetermined imaging sequence, and an image analyzer that detects presence or absence of a body motion of a subject under imaging using the plurality of the diffusion-weighted images.

The image analyzer comprises a group creator that creates a plurality of image groups each consisting of 6 or more diffusion-weighted images selected from a plurality of diffusion-weighted images so that the groups differ from one another in one or more of the included diffusion-weighted images, a diffusion index calculator that calculates value of a predetermined diffusion index representing characteristic amount of diffusion-weighted image for each image group from the diffusion-weighted images included in the image group, a body motion index calculator that calculates value of a predetermined body motion index relating to body motion information from the value of the diffusion index for each image group, and a body motion detector that determines presence or absence of body motion for each image group on the basis of the value of the body motion index.

Effect of the Invention

According to the present invention, in the measurement of DWI in which MPG is applied in many directions, body motion during imaging can be detected without prolonging imaging time.

BRIEF DESCRIPTION OF THE DRAWINGS

FIG. 5 is an explanatory drawing showing the operation of the group creator 301 of the first embodiment.

MODES FOR CARRYING OUT THE INVENTION

First Embodiment

Hereafter, the first embodiment of the present invention will be explained with reference to FIGS. 1 to 7. In all the drawings for explaining the embodiments of the present invention, the same numerical codes are attached to those having the same function, and repetition of the explanation thereof is omitted.

Figure 1:
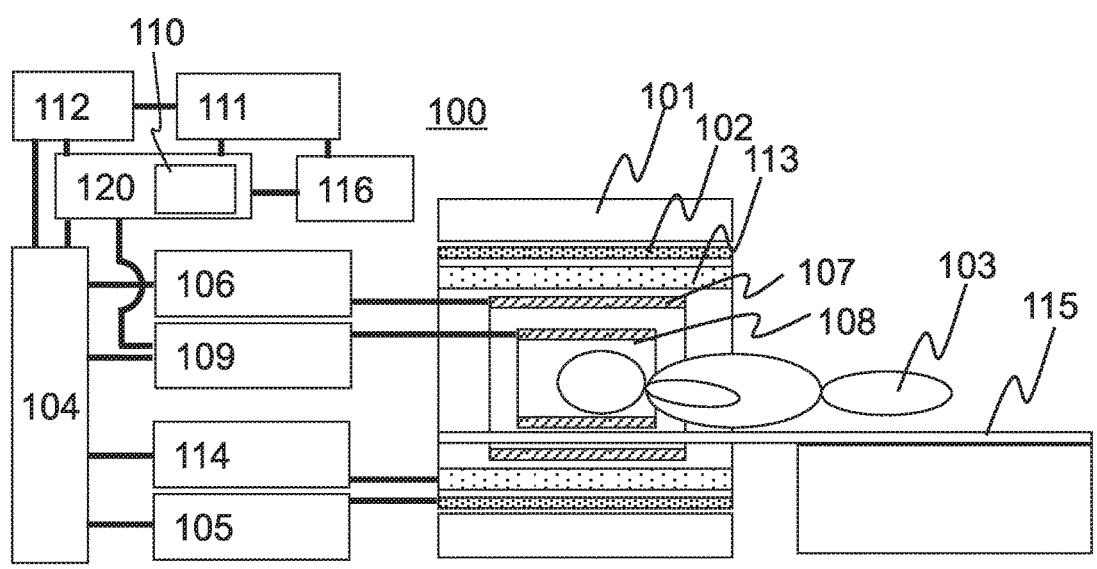
FIG. 1 is a block diagram showing the configuration of the MRI apparatus of the first embodiment.

As shown in FIG. 1, the MRI apparatus of this embodiment comprises a measurement part (101, 102, 107, 108, etc.) that acquires a plurality of diffusion-weighted images by applying diffusion gradient magnetic field pulses in a plurality of different directions defined beforehand according to a predetermined imaging sequence (refer to, for example, FIG. 2), and an image analyzer 110 that detects presence or absence of body motion of a subject under imaging using the plurality of the diffusion-weighted images.

Figure 3:
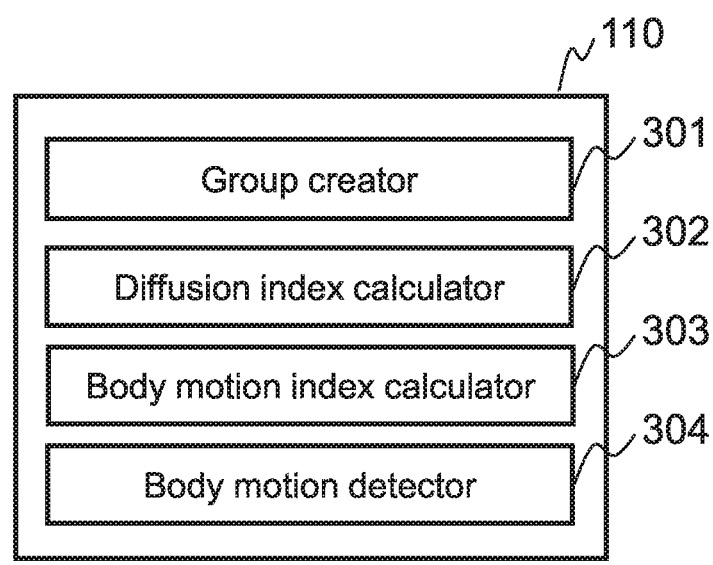
FIG. 3 is a functional block diagram of the image analyzer 110 of the first embodiment.
Figure 4:
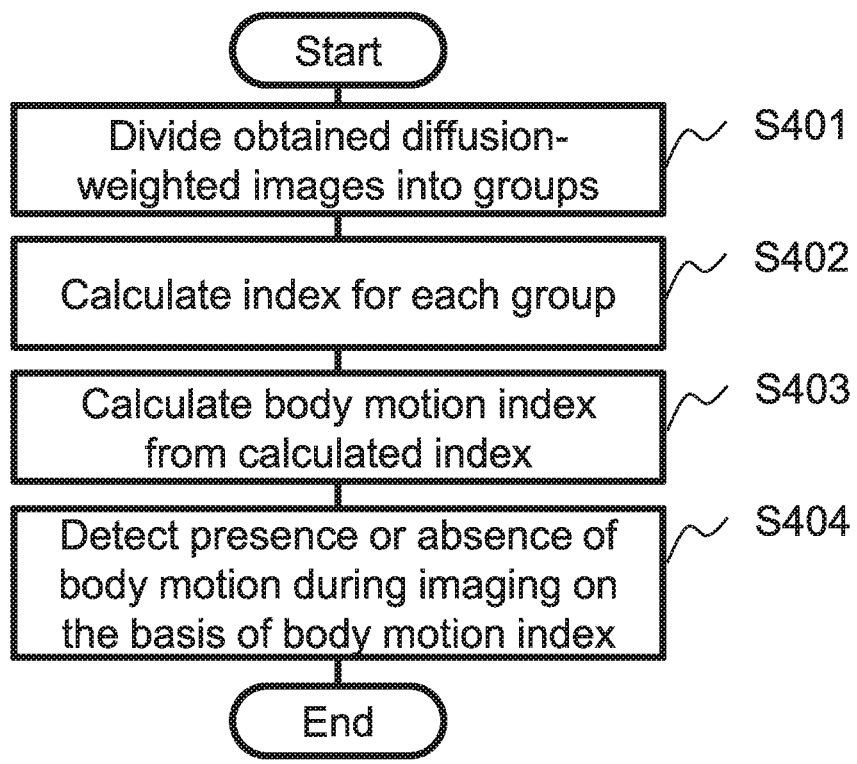
FIG. 4 is a flowchart showing the operation of the image analyzer 110 of the first embodiment.

As shown in FIG. 3, the image analyzer 110 comprises a group creator 301, a diffusion index calculator 302, a body motion index calculator 303, and a body motion detector 304. The group creator 301 creates a plurality of image groups 502, 503, etc. consisting of 6 or more diffusion-weighted images selected from a plurality of diffusion-weighted images 501 (refer to FIG. 5) obtained by the measuring part (101, 102, 107, 108, etc.) as shown in FIG. 4 so that the groups differ from one another in one or more of the included diffusion-weighted images. The diffusion index calculator 302 calculates value of an index defined beforehand that represents characteristic amount of diffusion-weighted image (diffusion index) for each of the image groups 502, 503, etc. from the diffusion-weighted images included in each image group. The body motion index calculator 303 calculates value of a body motion index defined beforehand concerning body motion information from the value of the diffusion index for each image group 502, 503, etc. The body motion detector 304 determines presence or absence of body motion for each image group on the basis of the value of the body motion index.

In the first embodiment, in order to obtain value of the index that represents characteristic amount of diffusion-weighted image for each image group consisting of 6 or more diffusion-weighted images chosen from a plurality of diffusion-weighted images as described above, 6 components (variables) of diffusion tensor represented by such a symmetric tensor of order 2 consisting of 3 rows and 3 columns as represented by the equation (1) mentioned below can be obtained by calculation from pixel values of the 6 or more diffusion-weighted images. That is, the diffusion directions (application directions of the diffusion gradient magnetic field pulses) of the 6 or more diffusion-weighted images do not need to be perpendicular to one another, and it is sufficient that they are arbitrary different directions. Therefore, it becomes possible to detect presence or absence of body motion from a combination of one diffusion-weighted image and 5 previously obtained diffusion-weighted images created at the time of obtaining every one diffusion-weighted image, and thus temporal resolution of the body motion detection can be improved.

[Equation 1]

$$D = \begin{pmatrix} D_{11} & D_{12} & D_{13} \\ D_{21} & D_{22} & D_{23} \\ D_{31} & D_{32} & D_{33} \end{pmatrix} \begin{matrix} D_{12} = D_{21} \\ D_{13} = D_{31} \\ D_{23} = D_{32} \end{matrix} \quad (1)$$

It is desirable that the diffusion directions of the 6 or more diffusion-weighted images constituting each image group are spatially uniformly distributed. This is because if a plurality of diffusion-weighted images of which diffusion directions are spatially uniformly distributed are used, the index that represents characteristic amount of diffusion-weighted image can be highly precisely calculated, and accuracy of detection of body motion is improved.

It is also desirable that the diffusion directions of all the diffusion-weighted images 501 measured by the measurement part (101, 102, 107, 108, etc.) are spatially uniformly distributed. This is because the calculation accuracy of MD or FA to be calculated after the measurement is thereby improved. In addition, when a plurality of image groups each consisting of 6 or more diffusion-weighted images of which diffusion directions are spatially uniformly distributed are formed, it becomes easier to create the groups so that diffusion directions of the images of each image group should be spatially uniform, and therefore accuracy of detection of body motion is improved.

Hereafter, the MRI apparatus of the first embodiment will be specifically explained. A magnetic resonance imaging (MRI) apparatus of this embodiment will be explained. The MRI apparatus 100 of this embodiment applies a radio frequency magnetic field on a subject 103 placed in a static magnetic field to excite nuclear magnetization in the subject 103, and measures generated magnetic resonance signals (echo signals). In this process, imaging (image acquisition) is attained by applying a gradient magnetic field to impart positional information to the magnetic resonance signals to be measured. FIG. 1 is a block diagram showing a typical configuration of the MRI apparatus 100 of this embodiment, which realizes the above process. The MRI apparatus 100 of this embodiment comprises a magnet 101 that generates a static magnetic field, a gradient coil 102 that generates a gradient magnetic field, an RF coil 107 that irradiates a radio frequency pulse (henceforth referred to as RF pulse) to a subject (living body) 103, an RF probe 108 that detects echo signals generated from the subject 103, and a bed (table) 115 on which the subject (for example, living body) 103 is placed in the static-magnetic field space generated by the magnet 101.

The MRI apparatus 100 of this embodiment further comprises a gradient magnetic field power supply 105 that drives the gradient coil 102, a radio frequency magnetic field generator 106 that drives the RF coil 107, a receiver 109 that receives the echo signals detected with the RF probe 108, a sequencer 104 that sends commands to the gradient magnetic field power supply 105 and the radio frequency magnetic field generator 106 to make them generate a gradient magnetic field and a radio frequency magnetic field, respectively, and sets a nuclear magnetic resonance frequency serving as a standard of the detection in the receiver 109, a computer 120 that performs signal processing for the detected signals to perform processing for reconstruction of image of the subject and so forth, a display 111 that displays results of the processing performed by the computer 120, a storage device 112 that stores the results of the processing, and an input device 116 that receives directions from an operator.

These parts of the MRI apparatus 100 constitute the aforementioned measurement part that obtains diffusion-weighted images.

The aforementioned image analyzer 110 is built in the computer 120 in order to detect body motion of the subject. The storage device and CPU are built in the computer 120, and the computer reads out programs stored beforehand in the storage device into CPU, and executes them to realize the functions of the image analyzer 110. It is also possible to realize all or a part of the functions of the computer 120 and the image analyzer 110 are realized by a general-purpose information processor provided independently from the MRI apparatus 100. In such a case, data are transmitted and received between the MRI apparatus 100 and the information processor.

In the MRI apparatus 100 having such a configuration as described above, an RF pulse is applied to the subject 103 by the RF coil 107, and a gradient magnetic field pulse for giving positional information such as those for slice selection and phase encoding to echo signals is applied by the gradient coil 102 under the control by the sequencer 104. The signals generated from the subject 103 are received by the RF probe 108, the detected signals are sent to the computer 120, and signal processing such as image reconstruction is performed in the computer 120. Not only results of the signal processing, the detected signals themselves, imaging conditions, and so froth may also stored in the storage device 112, as required.

When it is necessary to adjust uniformity of the static magnetic field, the MRI apparatus 100 may further comprise a shim coil 113 and a shim power supply 114 that drives the shim coil 113. The shim coil 113 comprises a plurality of channels, and generates an additional magnetic field that corrects non-uniformity of the static magnetic field with an electric current supplied from the shim power supply 114. The electric currents sent to the channels constituting the shim coil 113 at the time of adjustment of uniformity of the static magnetic field are controlled by the sequencer 104.

The sequencer 104 controls operations of the parts that constitute the MRI apparatus 100, and performs the measurement as described above, and it controls the parts so that they operate according to timing and intensity programmed beforehand. Among the programs mentioned above, one describing timing and intensities of the radio frequency magnetic field, gradient magnetic field, and signal reception is called imaging pulse sequence. The imaging (measurement of an image) is performed according to an imaging pulse sequence and imaging parameters required for controlling it. The imaging pulse sequence is prepared beforehand, and stored in the storage device 112. The imaging parameters are inputted by an operator via a user interface provided by the input device 116 and the display 111.

Figure 2:
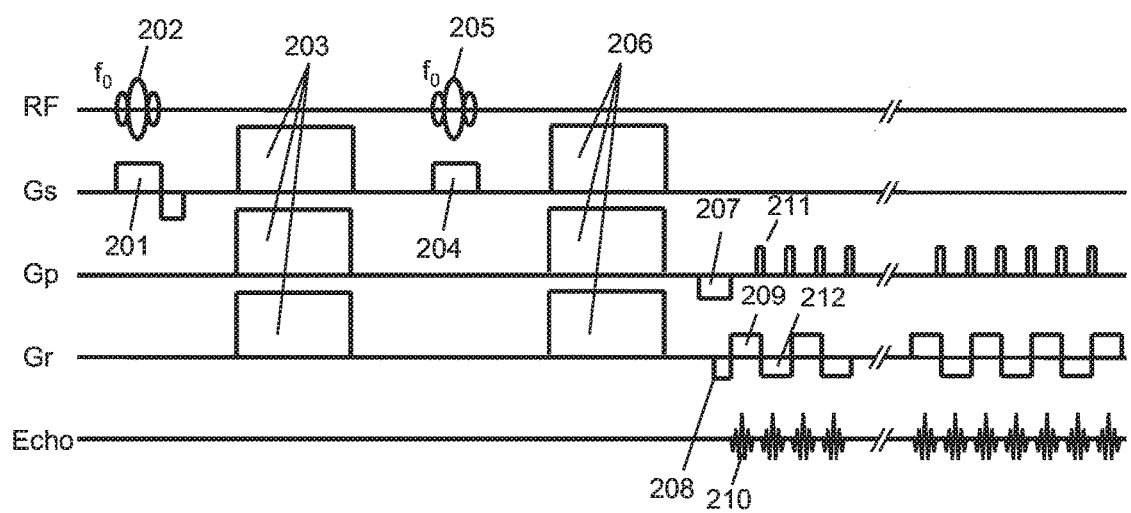
FIG. 2 is a time chart of an imaging pulse sequence for diffusion-weighted image.

A pulse sequence for ss-DWEPI (single shot Diffusion-weighted Echo Planar Imaging) is shown in FIG. 2 as an example of the imaging pulse sequence for obtaining diffusion-weighted image. The operation defined by this pulse sequence is as follows. An RF pulse 202 is applied at a resonance frequency $f_0$ of the objective nuclear magnetization with application of a gradient magnetic field pulse 201 of a slice direction (Gs) to induce the nuclear magnetic resonance phenomenon in nuclear magnetization in a certain slice of the subject 103.

Then, diffusion gradient magnetic field (motion probing gradient, henceforth referred to as MPG) pulses 203 for measuring random movement of nuclear magnetization are applied. The directions of the application of the MPG pulses 203 are set to be directions in which measurement of random motion of nuclear magnetization is desired.

Then, an RF pulse 205 for magnetization refocusing at the resonant frequency $f_0$ is applied with application of a slice gradient magnetic field pulse 204 to rephase the magnetization of which phases are diffused by the non-uniformity of the static magnetic field.

Then, MPG pulses 206 are applied to refocus the phase of nuclear magnetization without motion, which is diffused by the MPG pulses 203.

Then, after a phase encoding gradient magnetic field pulse 207 for imparting positional information for the phase encoding direction (Gp) to the phase of magnetization, and a read-out gradient magnetic field pulse 208 for dephasing are applied, a magnetic resonance signal (echo) 210 is measured with applying a read-out gradient magnetic field pulse 209 for imparting positional information for the read-out direction (Gr). Thereafter, an operation of applying a phase encoding gradient magnetic field pulse 211, applying an inversed read-out gradient magnetic field pulse 212, and measuring the magnetic resonance signal (echo) 210 is repeated with varying phase encoding amount. Echoes in a number required for reconstructing one image are thereby obtained.

The computer 120 executes a predetermined image reconstruction program to arrange the echoes in the k-space, and reconstruct an image by two-dimensional inverse Fourier transform. One diffusion-weighted image is thereby obtained.

The sequencer 104 used in this embodiment repeatedly executes the aforementioned pulse sequence with changing the application direction of the MPG pulse 206 and b value, and measures a desired number of diffusion-weighted images. An image for a b value of 0, which means that the MPG pulse 206 is not applied, may be measured if needed, although it is not necessarily required for detection of body motion.

Number of diffusion-weighted images to be measured, diffusion directions (MPG application directions) of the diffusion-weighted images, and b value are inputted by an operator into the computer 120 via the input device 116 like the other imaging parameters. As described above, it is desirable that spatial distribution of the diffusion directions (MPG application directions) of all the diffusion-weighted images to be measured is uniform. For realizing this, a plurality of spatially uniformly distributed MPG application directions determined beforehand are stored in the storage device 112 for each number of diffusion-weighted images that can be inputted by the operator. According to the number of the diffusion-weighted images inputted from the input device 116, the computer 120 reads out a plurality of spatially uniformly distributed MPG application directions from the storage device 112, and sets them in the sequencer 104.

The user interface may also be constituted so that the operator can input a desired MPG application direction for every diffusion-weighted image to be measured. The MPG application direction can be set by, for example, inputting components for the x-axis, y-axis, and z-axis directions in the device coordinate. The sequencer 104 can also be constituted so that the MPG application direction for every diffusion-weighted image to be measured is received from the operator via the input device 116, and an MPG pulse is applied in that direction.

The user interface may also be constituted so that a plurality of values can be inputted as the b value. In such a case, the number of the MPG application directions is set to be the same for each b value.

Hereafter, there will be specifically explained an operation of the image analyzer 110 for detecting presence or absence of body motion during imaging in a plurality of diffusion-weighted images reconstructed by the computer 120.

As described above, the image analyzer 110 comprises the group creator 301, diffusion index calculator 302, body motion index calculator 303, and body motion detector 304 (refer to FIG. 3). The functions of these parts can be realized by executing programs stored beforehand in the storage device built in the computer 120 with CPU also built in the computer 120, or can be realized with hardware using a programmable IC such as ASIC (application specific integrated circuit) and FPGA (field-programmable gate array).

The flow of the processing performed by the image analyzer 110 is shown in FIG. 4. First, the group creator 301 chooses 6 or more diffusion-weighted images from a plurality of diffusion-weighted images reconstructed by the computer 120 to create image groups (step S401). In this group creation, although a certain diffusion-weighted image may be repeatedly included in a plurality of groups, the image groups are formed so that each image should certainly included in any of the groups.

A specific example of the group creation method carried out by the group creator 301 will be explained below with reference to FIGS. 5 and 6. As shown in FIG. 5, sequential numbers are assigned to a plurality of the measured diffusion-weighted images 501. For example, sequential numbers are assigned in the order of image acquisition. When body motion is detected as a post treatment after obtaining all the diffusion-weighted images 501, the plurality of the diffusion-weighted images 501 may be rearranged in a desired order, and then sequential numbers may be assigned to them. Then, 6 images are chosen from the first one in the order of the sequential numbers (from No. 1 to No. 6) to create an image group 502 with the selected 6 diffusion-weighted images. Setting aside the first diffusion-weighted image (No. 1), 6 images are chosen in the order of the sequential numbers (from No. 2 to No. 7) to create an image group 503. Similarly, with repeatedly setting aside a diffusion-weighted image of the smallest number, 6 images are chosen in the order of the sequential numbers to form image groups 504 to 510, respectively. The diffusion-weighted images once set aside are not included in image groups to be newly created, and a group 514 of the image groups is created so that all the obtained images should be included in at least one group.

As for the image groups 502 to 510, it is desirable that spatial distribution of the diffusion directions (MPG application directions) of the included diffusion-weighted images is substantially similar among the image groups, and it is especially desirable that spatial distribution of the MPG application directions of the diffusion-weighted images included in each of the image groups 502 to 510 is uniform. The accuracy of the detection of body motion mentioned later can be improved by such a characteristic. Therefore, it is desirable that the group creator 301 evaluates spatial uniformity of the MPG application directions of the diffusion-weighted images included in each of the image groups, and chooses diffusion-weighted images so that the evaluation value should be a value that indicates that the uniformity is not lower than a predetermined level.

As the method performed by the group creator 301 for evaluating spatial uniformity of the MPG application directions of the diffusion-weighted images, there is a method of performing the evaluation using the following equation (2). In the following equation (2), m represents number of images in a group, and n represents application direction of MPG of diffusion-weighted images of each group.

[Equation 2]

$$H = \frac{1}{m^2} \sum_{i=1}^{m} \sum_{j=1}^{m} \arccos \left| \frac{n_i \cdot n_j}{\|n_i\| \|n_j\|} \right| \qquad (2)$$

H in the equation (2) represents average value of angles formed by the MPG application directions, and a larger value indicates higher space uniformity. Therefore, the group creator 301 chooses the diffusion-weighted images of the image groups 502, 503, etc. so that H obtained in accordance with equation (2) should become larger than a value defined beforehand. The spatial distributions of the MPG application directions of the diffusion-weighted images included in the image groups 502, 503, etc. are thereby made substantially similar, or the spatial distribution can be thereby made uniform in each group.

However, when sequential numbers are assigned, and the image groups 502, 503, etc. are created by choosing images in the order of the sequential numbers as shown in FIG. 5, it is desirable that the diffusion-weighted images are rearranged beforehand so that the spatial distributions of the MPG application directions of the image groups 502, 503, etc. may become similar, or the spatial distribution in each image group becomes uniform.

When sequential numbers are assigned in the order of image acquisition, and the image groups 502, 503, etc. are created as shown in FIG. 5, it is also possible to obtain application order for the MPG application directions beforehand by calculation so that the spatial distributions of the MPG application directions of the image groups 502, 503, etc. become similar, or the spatial distribution in each image group becomes uniform, and store them in the storage device 112. The computer 120 reads out MPG application directions and application order of them from the storage device 112, sets them in the sequencer 104 according to the number of the diffusion-weighted images inputted from the input device 116, and performs imaging. If the group creator 301 creates image groups as shown in FIG. 5, the spatial distributions of the MPG application directions of the image groups 502, 503, etc. can be made similar, or the spatial distribution in each image group can be made uniform.

Figure 7:
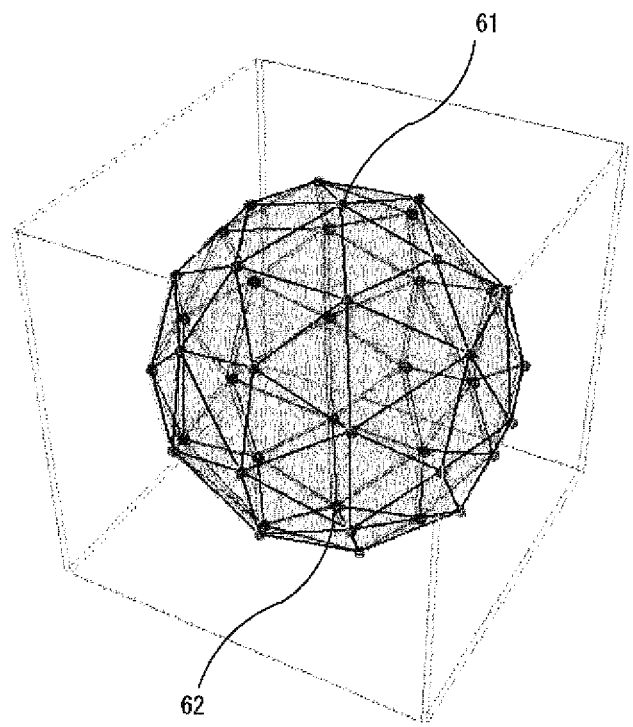
FIG. 7 is an explanatory drawing showing an example of the method for evaluating spatial uniformity of the MPG application directions of the first embodiment.

As the method performed by the group creator 301 for evaluating the spatial uniformity of the MPG application directions of the image group 502, 503, etc., the following method can also be employed. First, as shown in FIG. 7, a coordinate 61 for a unit vector of the MPG application direction of one diffusion-weighted image in an image group, and an origin symmetric coordinate thereof 62 are arranged in a space. Similarly, coordinates of the MPG application directions of all the diffusion-weighted images in an image group are similarly arranged in the space. A triangle mesh is formed by using all the arranged coordinates 61 etc. of the MPG application directions and origin symmetric coordinates thereof 62 etc. as nodal points as shown in FIG. 7. It is created by using, for example, the Delaunay triangulation, or the like. Since all the unit vector coordinates and origin symmetric coordinates thereof are points existing on a sphere having a radius of 1, mesh is not created in the inside, but only a surface mesh is created. A polyhedron constituted by the surface mesh of which nodal points are coordinates of unit vectors of the MPG application directions in each diffusion-weighted image of an image group is created as shown in FIG. 7. For example, when the number of the diffusion-weighted images in the image group is 6, an icosahedron is created. Then, the group creator 301 calculates volume V of the polyhedron that is constituted by the created surface mesh. As the spatial uniformity of the MPG application directions of the image group becomes higher, the volume V of the polyhedron becomes closer to the volume of sphere, and therefore spatial uniformity of the MPG application directions of each group can be evaluated on the basis of ratio of the volume of the sphere and the volume V of the polyhedron as shown in the following equation (3).

[Equation 3]

$$R = \frac{3V}{4\pi} \quad (3)$$

This equation is for the case where the radius of the sphere is 1. The group creator 301 chooses diffusion-weighted images to create image groups so that R in the equation (3) should be not smaller than a threshold defined beforehand. Image groups can be thereby created with uniform spatial distribution of MPG application directions. In consideration that the polyhedron formed by the mesh is a regular polyhedron when the MPG application directions are uniform, the threshold is set to be a value near the ratio of volume of sphere and volume of a regular polyhedron.

A ratio of the surface area of the obtained polyhedron and the surface area of the sphere may be obtained instead of using the equation (3). Also in such a case, image groups can be created with uniform spatial distribution of MPG application directions by choosing diffusion-weighted images to create the image groups so that the ratio should be not smaller than a threshold defined beforehand.

Then, in the step S402, the diffusion index calculator 302 shown in FIG. 3 calculates value of a predetermined index that represents characteristic amount of diffusion-weighted image (referred to as diffusion index in this explanation) using all the diffusion-weighted images included in the group for each of the image groups 502, 503, etc. (refer to FIG. 6). It is desirable that the predetermined index is an index concerning diffusion. Specifically, at least one of the mean diffusivity (MD) and diffusion fractional anisotropy (FA) can be used. In this description, an example in which the diffusion index value is calculated for all pixels of a diffusion-weighted image to generate a diffusion index value image will be explained. However, it is also possible to obtain the diffusion index values only for pixels in a region of interest, pixels of which signal intensities are higher than a certain value, or pixels of a predetermined region (for example, region corresponding to ¼ of the whole image).

In this embodiment, the diffusion index calculator 302 calculates a false mean diffusivity MD as the diffusion index in accordance with the equations (4) and (5) mentioned below. It is known that when the diffusion factor (b value) of MPG pulse is b, pixel value of diffusion-weighted image $S(n,b)$ can be obtained by using a pixel value $S_0$ of an image obtained without application of MPG pulse (b=0), MPG application direction n, and component $D_{ij}$ of diffusion tensor (refer to the equation (1)) in accordance with the equation (4).

[Equation 4]

$$S(n, b) = S_0 \text{Exp}\left(-b\sum_{i=1}^{3}\sum_{j=1}^{3} n_i n_j D_{ij}\right) \quad (4)$$

The diffusion index calculator 302 can calculate 6 components of the diffusion tensor D represented by the equation (1) by calculating the equation (4) using pixel values of 6 or more diffusion-weighted images of an image group, b value at the time of imaging, MPG application direction n, and a predetermined constant $S_0$ common to all the pixels. Since the diffusion tensor D is a symmetric tensor of order 2, remaining 3 components are the same as 3 components among the obtained 6 components. In this example, a predetermined constant common to all the pixels, for example, a constant larger than the maximum of the pixel values of all the measured images, is used as $S_0$ so that the influence of images wherein the b value is 0 can be disregarded. Therefore, the component $D_{ij}$ of the diffusion tensor to be obtained is an approximated value, and therefore it is referred to as false component $D_{ij}$ of diffusion tensor in this explanation.

Then, the diffusion index calculator 302 calculates characteristic values $\lambda_1$, $\lambda_2$, and $\lambda_3$ ($\lambda_1 > \lambda_2 > \lambda_3$) using the obtained components of the false diffusion tensor D. The mean diffusivity MD is calculated by using the calculated characteristic values in accordance with the equation (5). Since the false diffusion tensor is used in this calculation, the calculated mean diffusivity MD is referred to as false mean diffusivity MD. As described above, the diffusion index calculator 302 can calculate the false mean diffusivity MD as the diffusion index of the diffusion-weighted images for each of the image groups 502, 503, etc.

[Equation 5]

$$MD = \frac{\lambda_1 + \lambda_2 + \lambda_3}{3} \quad (5)$$

When there is no body motion during the imaging, it can be expected that the value of MD calculated for a certain image group (for example, 502) will be the same as the value of MD calculated for corresponding pixels of another image group (for example, 503, etc.). Therefore, the diffusion index calculator 302 can also calculate, as the diffusion index, a false diffusion fractional anisotropy FA, which can be calculated in accordance with the following equation (6).

[Equation 6]

$$FA = \sqrt{\frac{3}{2} \frac{(\lambda_1 - MD)^2 + (\lambda_2 - MD)^2 + (\lambda_3 - MD)^2}{\lambda_1^2 + \lambda_2^2 + \lambda_3^2}} \quad (6)$$

In the aforementioned explanation, a predetermined constant common to all the pixels is used as $S_0$ when the diffusion index calculator 302 calculates the equation (4) so that the influence of images where the b value is 0 can be disregard, but this embodiment is not limited to such a calculation method. When an imaging pulse sequence for diffusion-weighted image is executed, an image where the b value is 0 may also be obtained, and pixel values thereof may be used as $S_0$. In such a case, MD or FA calculated in accordance with the equation (5) or (6) is the mean diffusivity MD or diffusion fractional anisotropy FA itself based on assumed normally distributed three-dimensional elliptic diffusion distribution. Therefore, it is not necessary to separately calculate the mean diffusivity MD and diffusion fractional anisotropy FA for evaluation of diffusion of the diffusion-weighted image, and thus computational cost can be reduced.

Then, in the step S403, the body motion index calculator 303 shown in FIG. 3 calculates value of the body motion index, which varies depending on magnitude of body motion, from the diffusion index calculated for every pixel for each of the image groups 502, 503, etc. in the step S402. First, all the combinations of two image groups that can be selected from the image groups created in the step S401 (sets of image groups) are created. Difference of the values of the diffusion index obtained for every pixel in the step S402 is obtained for the corresponding pixels of the image groups of each combination. This calculation is performed for all the pixels for which the diffusion index value is calculated in the step S402. Square root of average root mean square of the obtained difference values for all the pixels is calculated, and this is used as a body motion index. The standard deviation of the difference values may also be used as the body motion index.

Then, in the step S404, the body motion detector 304 shown in FIG. 3 determines whether there is body motion during acquisition of a series of plurality of diffusion-weighted images 501 (FIG. 5) on the basis of the body motion index obtained in the step S404 (step S404). As the method for detecting presence or absence of body motion performed by the body motion detector 304, for example, there is used a method of comparing the body motion index values of all the sets of the image groups obtained in the step S403 and a threshold determined beforehand, and judging that there is body motion during the imaging when there is a set of which index value exceeds the threshold (or there is a set of which index value does not exceed the threshold). The threshold can be set with reference to values of body motion index for groups consisting of diffusion-weighted images obtained in a state that there is no body motion.

The body motion detector 304 displays the result of the detection of presence or absence of body motion on the display ill, and thereby presents it to a user. This makes the operator possible to know presence or absence of the body motion, of which determination is difficult only from diffusion-weighted image as in conventional techniques, and therefore the operator can determine whether re-imaging is performed or not. Alternatively, it is also possible to employ such a configuration that when there is body motion during the imaging, re-imaging is automatically performed. In such a case, the operator does not need to perform any operation for re-imaging, and therefore burden of the operator is eased.

The method for calculating the body motion index used in the step S403 is not limited to the aforementioned method. For example, as shown in FIG. 6, an image of diffusion index value created for a specific image group is used as a reference, difference values are obtained for every pixels between the image of the reference and images of diffusion index value of image groups other than that of the reference, and square root of average root mean square of the difference values or the like may be obtained, and used as the body motion index. Mutual information amount, difference value of images, normalized cross-correlation, or the like may be calculated between an image of diffusion index value of an image group of the reference and images of diffusion index value of other image groups other than the reference can also be calculated, and used as the body motion index.

It is also possible to use an image of diffusion index value obtained by using all the diffusion-weighted images 501 (FIG. 5) as the reference. It is also possible to use an image obtained with b value of 0 as the reference.

There is explained above an example where the body motion index is calculated for all the pixels of the diffusion-weighted images of each image group in the aforementioned step S402, and the body motion index is calculated from the obtained image of diffusion index value in the steps S403 and 404. However, the diffusion index calculator 302 may calculate the diffusion index only for a part of the pixels in the step S402. In such a case, computational complexity is decreased, and therefore processing time required until detection of body motion can be shortened. Therefore, it provides an advantage that detection result can be notified earlier.

As explained above, in the first embodiment, a plurality of image groups are created by choosing 6 or more diffusion-weighted images obtained by execution of an imaging pulse sequence, and presence or absence of body motion during imaging is detected. Therefore, body motion can be detected from the image groups of diffusion-weighted images in which the diffusion directions are not perpendicular to one another, thus image groups can be created for every imaging to detect presence or absence of body motion, and temporal resolution of body motion detection can be improved. Accordingly, body motion can be detected in a short period of time, or when an inexplicable image is obtained in diagnosis, whether the cause of the inexplicableness is artifact due to body motion can be determined, and therefore improvement in diagnostic ability can be expected.

Second Embodiment

Hereafter, the second embodiment of the present invention will be explained.

Figure 8:
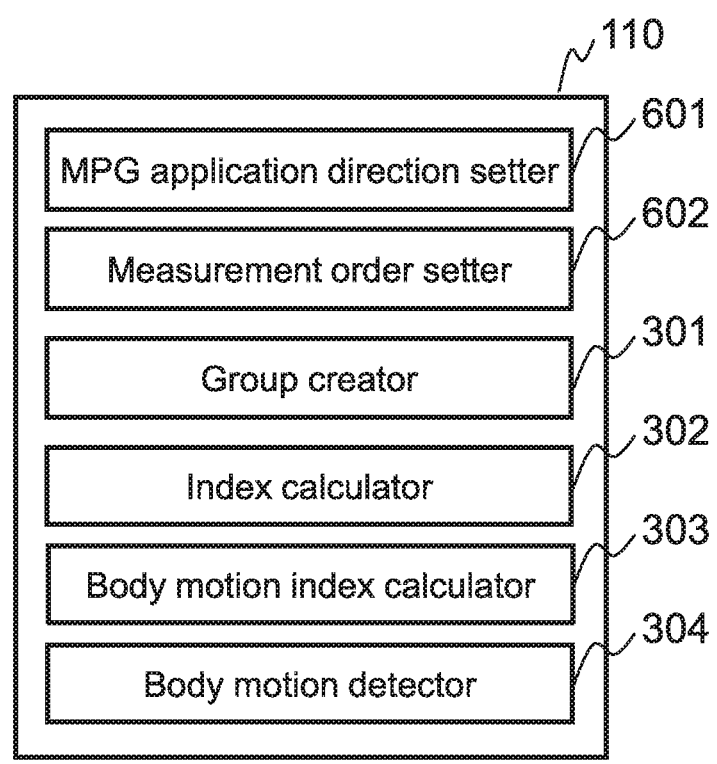
FIG. 8 is a functional block diagram of the image analyzer 110 of the second embodiment.

As shown in FIG. 8, the MRI apparatus of the second embodiment comprises an MPG application direction (diffusion direction) calculator 601 that obtains a plurality of spatially uniformly distributed diffusion directions (MPG application direction) according to the number of the diffusion-weighted images to be obtained, for example, set by an operator. The apparatus further comprises a measurement order setter 602 that sets order of diffusion directions for which imaging should be performed in the measurement part (101, 102, 107, 108 etc. (refer to FIG. 1)).

The measurement order setter 602 arranges a plurality of diffusion directions (MPG application directions) obtained by the diffusion direction calculator 601 in order, repeatedly performs an operation of choosing a predetermined number not smaller than 6 of consecutive diffusion directions with shifting the first direction of the directions to be selected one by one to create a plurality of sets of diffusion directions, rearrange the plurality of diffusion directions so that spatial distribution of the diffusion directions should become uniform in each set, and determines the order of the rearranged diffusion directions to be the order of diffusion directions for which imaging should be performed.

The group creator 301 can choose a plurality of images corresponding to the plurality of the sets set by the measurement order setter 602 from a plurality of diffusion-weighted images obtained by the measurement part (101, 102, 107, 108 etc.) in the aforementioned order to create a plurality of image groups 502, 503, etc. in which diffusion directions are spatially uniform. Specifically, it repeats an operation of choosing a predetermined number not smaller than 6 of consecutive diffusion directions with shifting the first direction of the directions to be chosen one by one to create a plurality of image groups.

Since the configurations of the other parts of the MRI apparatus of the second embodiment are basically the same as those of the first embodiment, explanation will be focused on the configurations different from those of the first embodiment, and operations thereof will be explained.

Figure 9:
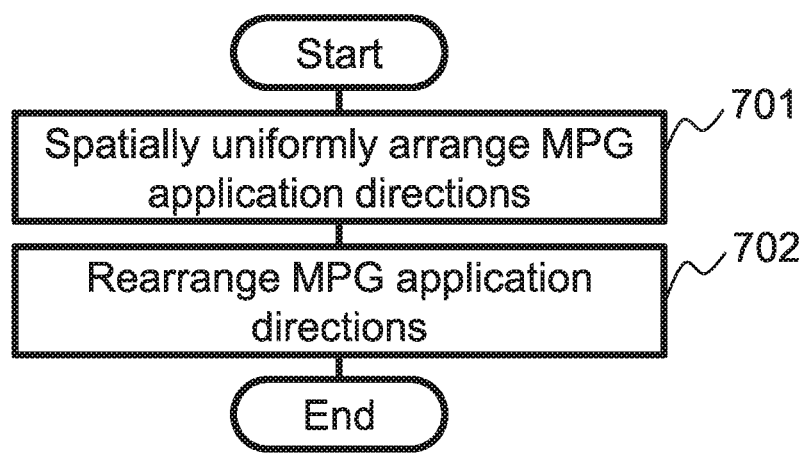
FIG. 9 is a flowchart showing a part of the operation of the image analyzer 110 of the second embodiment.

A part of the flow of the processing performed by the computer 120 is shown in FIG. 9. First, the MPG application directions defined in the imaging sequence for obtaining diffusion-weighted images are set by the MPG application direction setter 601 (step S701). Then, order of the measurement for the MPG application directions set above is set by the measurement order setter 602 (step S702).

The method for setting the application directions performed by the MPG application direction setter 601 will be specifically explained below. First, number t of the diffusion-weighted images to be obtained is set by, for example, receiving it from an operator. Since this number is the number t of application directions desired to be set, t of spatially uniform application direction components are calculated. The procedure is as follows.

First, one fixed point is set. Here, a fixed point is arranged at $P_0=(0, 0, 1)$ as an example. Then, points $P_i$ ($i=1, \ldots t-1$) are arranged at random on the surface of sphere according to the number t of the application directions desired to be set. Points origin-symmetric to the points $P_i$ are defined to be $Q_i$ ($=-P_i$). Since the application directions should be independently defined, in order to calculate spatially uniform components, origin-symmetric points are also arranged to take spatial uniformity of the points including origin-symmetric points into consideration. For the randomly arranged points $P_i$ other than the fixed point $P_0$, values calculated from unit vectors connecting the points $P_i$ and other points $P_j$ and $Q_j$ weighted with distances are defined as repulsive forces $F_i$, and calculated in accordance with the equation (7).

[Equation 7]

$$F_i = \frac{1}{2t-2}\left(\sum_{j=0}^{t-1} \frac{(P_i - P_j)}{|P_i - P_j|} w_{p,j} + \sum_{j=0}^{t-1} \frac{(P_i - Q_j)}{|P_i - Q_j|} w_{q,j}\right) \quad (7)$$

$$w_{p,j} = \frac{(1-\delta_{i,j})}{|P_i - P_j|}, \; w_{q,j} = \frac{(1-\delta_{i,j})}{|P_i - Q_j|}, \; \delta_{i,j} = \begin{cases} 1(i=j) \\ 0(i \neq j) \end{cases}$$

Then, updated points $P_i'$ of $P_i$ are calculated from the repulsive forces $F_i$ in accordance with the following equation (8).

[Equation 8]

$$P_i' = \frac{0.5(P_i + F_i)}{|0.5(P_i + F_i)|} \quad (8)$$

The calculation for each of the updated points $P_i'$ of $P_i$ in accordance with the equation (8) is repeated until angle θ of the each repulsive force $F_i$ and each point $P_i$ calculated in accordance with the following equation (9) becomes substantially 0 (θ<10$^{-8}$), that is, they become almost parallel to each other.

[Equation 9]

$$\theta = \sum_{i=1}^{t-1} \arccos\left|\left(\frac{P_i \cdot F_i}{|P_i||F_i|}\right)\right| \quad (9)$$

Points $P_i$ can be arranged at points of which distances from other points are balanced well.

According to the aforementioned method, the MPG application direction setter 601 can arrange n of points $P_0$ and $P_i$ (I=1, ... t-1) of which distances between one another are balanced well, and define the directions connecting the starting point and n of points $P_0$ and $P_i$ as the MPG application directions to thereby set substantially spatially uniformly arranged MPG application directions.

Hereafter, the method for setting measurement order for the MPG application directions performed by the measurement order setter 602 will be specifically explained. All the permutations of t of the MPG application directions set by the MPG application direction setter 601 are created, and image groups are successively created in the order from the first one as shown in FIG. 5. Then, a permutation that gives the highest average value of the spatial uniformity of the MPG application directions in each group is chosen, and the order in this group is used as the measurement order for the MPG application direction. For the calculation of the spatial uniformity, the aforementioned method for calculating spatial uniformity on the basis of the volume ratio defined by the aforementioned equation (3) can be used.

When the method for setting measurement order for the MPG application direction is performed by creating all the permutations of t of MPG application directions, and successively creating image groups from the first one is performed, the number of the permutations may become huge. In such a case, the following method can be alternatively performed, in which the measurement order is set for the permutations beforehand in the order of the spatial uniformity from the highest. First, the measurement order setter 602 creates all combinations of 6 MPG application directions chosen from t of MPG application directions set by the MPG application direction setter 601. For all the created combinations, spatial uniformity is calculated. For the calculation of the spatial uniformity, the method based on the volume ratio calculated in accordance with the aforementioned equation (3) can be used. Then, all the combinations each of which obtained spatial uniformity exceeds a threshold defined beforehand are extracted. For example, the threshold may be set to be 0.55 because a spatial uniformity is about 0.605 in the case of icosahedron.

Then, in one of the extracted combinations, all sequences each consisting of 6 MPG application directions as the components (candidates of the order of the first to sixth measurements) are created as permutations.

In one of the created sequences of the candidates of the measurement order, the heading (first) MPG application direction is excluded. Then, one MPG application direction is chosen from the MPG application directions not included in the combination (t-6 of directions), and added to the sequence of the remaining 5 MPG application directions (second to sixth directions) to create a combination consisting of 6 MPG application directions. Spatial uniformity is calculated for the 6 MPG application directions constituting the created combination. The operation of calculating the spatial uniformity is repeated with changing the one MPG application direction to be added within the (t-6) of the MPG application directions, and an MPG application direction that gives the highest spatial uniformity is obtained. This obtained MPG application direction is determined to be the seventh element of the sequence of the measurement order. The 8th to t-th MPG application directions are successively determined in a similar manner.

The processing for determining the 7th to t-th MPG application directions is similarly performed for all the other sequences (first to sixth sequences) of the candidates of the measurement order. By this processing, there are created, for one combination giving a spatial uniformity not smaller than the threshold, a plurality of candidates of the measurement order for t of the MPG application directions, in which the 6 MPG application directions included in the combination correspond to the first to sixth measurement orders. By performing this processing for all the combinations that give a spatial uniformity not smaller than the threshold, a plurality of candidates of the measurement order of t of the MPG application directions can be created for each combination.

Then, for each of the plurality of the created candidates of the measurement order, image groups of diffusion-weighted images are successively created from the first image as shown in FIG. 5, and average of the spatial uniformities of the MPG application directions is calculated in each image group. Among these candidates, the candidate of the measurement order that gives the highest average of the spatial uniformity is determined as the measurement order for the MPG application direction. This method can reduce computational complexity compared with the method of creating all the permutations of t of MPG application directions, and successively creating image groups from the first one to set the measurement order for the MPG application direction.

It is also possible to optimize the measurement order for the MPG application direction chosen from the plurality of the candidate of the measurement order and the MPG application directions thereof by further fine adjustments. For example, fine adjustments are performed for the determined measurement order and MPG application directions thereof as the initial conditions with amounts preliminarily determined for the measurement order and MPG application direction, and sum of average of spatial uniformities for the MPG application direction of respective image groups, which are successively created from the first one for the finely adjusted measurement orders for the MPG application direction, and spatial uniformities of all the application directions is calculated. The amounts of the fine adjustments are determined by an optimization method such as the downhill simplex method, so that the sum is maximized. The MPG application directions and measurement order therefor to which the determined amounts of fine adjustments are added are used as the optimized MPG application directions and measurement order therefor. The spatial uniformity in the groups created according to the measurement order can be thereby increased with maintaining the spatial uniformity of the MPG application directions, and improvement in accuracy of the detection of body motion can be expected.

In the second embodiment, the sequencer 104 executes an imaging pulse sequence according to the order for the MPG application direction set by the measurement order setter 602 to obtain a plurality of diffusion-weighted images. The image analyzer 110 detects presence or absence of body motion during imaging in the same manner as that of the steps S401 to S404 of the first embodiment shown in FIG. 4.

Figure 6:
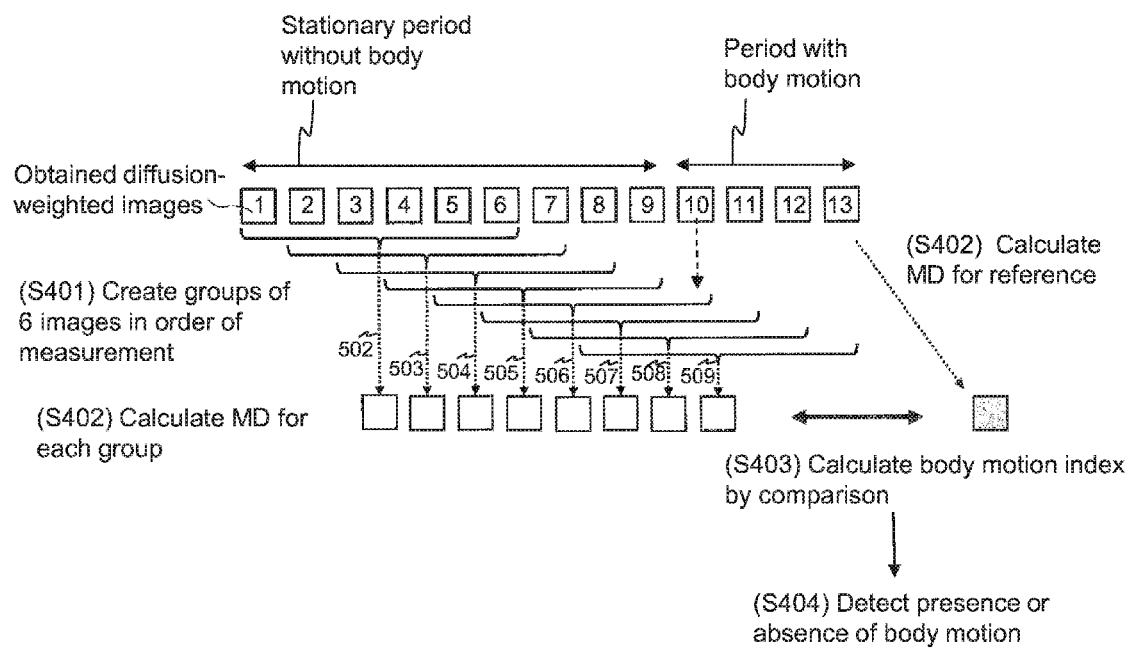
FIG. 6 is an explanatory drawing showing the operation of the image analyzer 110 of the first embodiment.

In the above operation, the group creator 301 used in the second embodiment assigns sequential numbers to the diffusion-weighted images in the order of measurement, chooses 6 consecutive images from the first diffusion-weighted image to create an image group, and then choose 6 consecutive images from the second diffusion-weighted image to create an image group, as shown in FIGS. 5 and 6. That is, there is used the method of creating image groups with successively shifting the first image. When the image groups are created as described above, the measurement order setter 602 sets the measurement order for the MPG application direction so that the spatial distributions of the MPG application directions of the diffusion-weighted images included in the image groups become uniform, and therefore the MPG application direction distribution in each image group can be made uniform.

Figure 10:
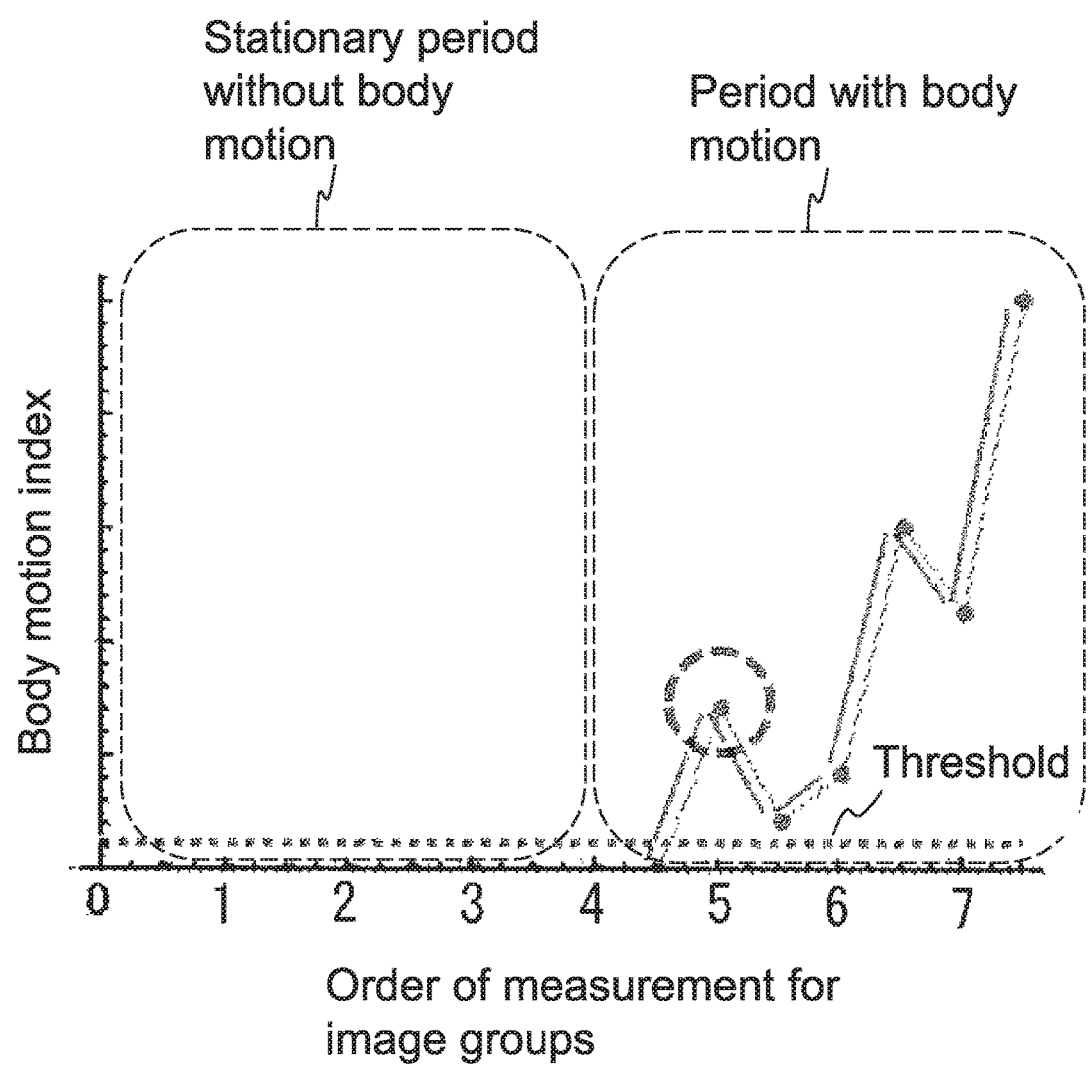
FIG. 10 is an explanatory drawing showing determination for body motion based on body motion index and threshold according to the second embodiment.
Figure 11:
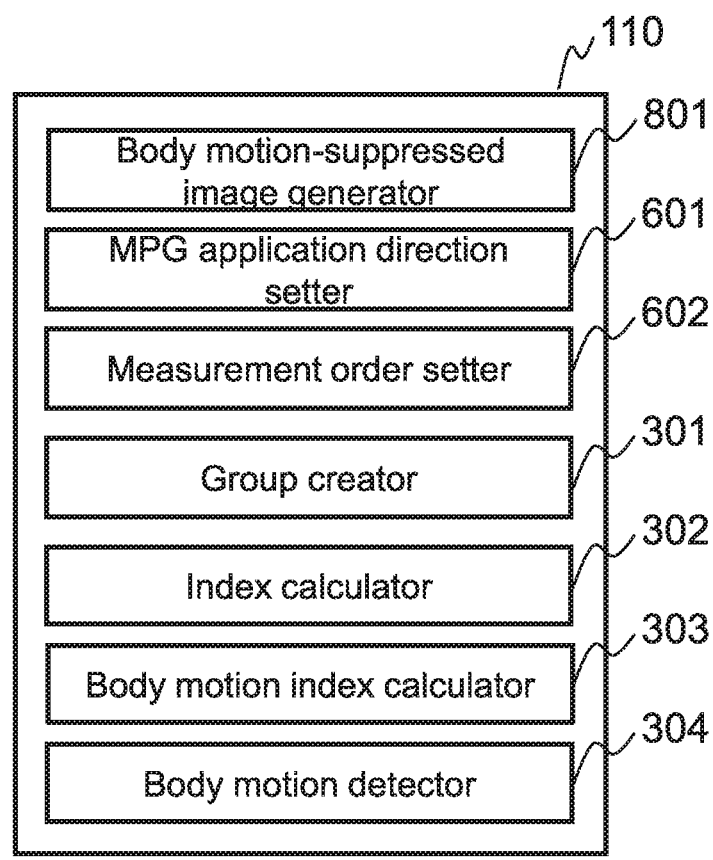
FIG. 11 is a functional block diagram of the image analyzer 110 of the third embodiment.

When the image groups 502 etc. are created as shown in FIGS. 5 and 6, diffusion-weighted images included in two consecutive image groups differ only in one image. Therefore, as explained for the first embodiment, if a diffusion index (for example, MD) is calculated for each image group in the step S402, and a body motion index (for example, absolute value of a value obtained by differentiating square root of average root mean square of difference in the measurement order) is obtained from comparison of the diffusion index of the reference and the diffusion index of the image group in the step S403, it may be judged that the values of the body motion index of the first to the fourth image groups 502 to 505 are lower than the threshold, thus there is not body motion, but the value of the body motion index of the fifth image group 506 exceeds the threshold, and therefore there is a body motion, as shown in FIG. 10.

In such a case, the body motion detector 304 can detect that body motion occurred at the time of obtaining the diffusion-weighted image that is not included in the fourth image group 505, but is included in the fifth image group 506 (10th image). The body motion detector 304 can thereby detect not only presence or absence of body motion, but also time of occurrence of body motion.

As explained above, according to this embodiment, because the image analyzer 120 comprises the MPG application direction setter 601 and the measurement order setter 602, only by receiving the number of diffusion images to be obtained from an operator, a group showing a high spatial uniformity of MPG application directions can be created, and improvement in accuracy of detection of body motion can be expected. The body motion detector 304 enables detection of not only presence or absence of body motion, but also time of occurrence of body motion.

Third Embodiment

Hereafter, the third embodiment of the present invention will be explained. The MRI apparatus of the third embodiment further comprises a body motion-suppressed image generator 801 in the image analyzer 110, as shown in FIG.

11. The configurations of the other parts are the same as those of the second embodiment.

Figure 12:
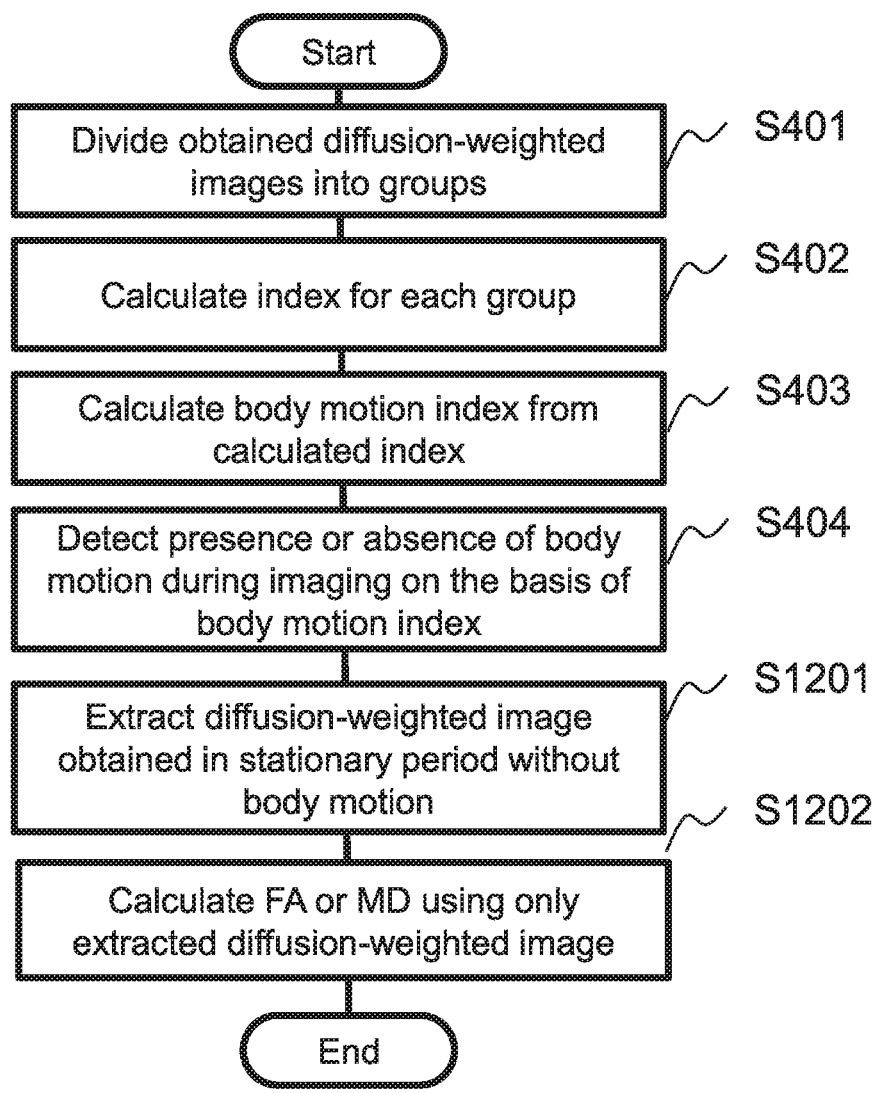
FIG. 12 is a flowchart showing the operation of the image analyzer 110 of the third embodiment.

As shown in FIG. 12, the image analyzer 110 of the third embodiment performs the step S401 to S404 as shown in FIG. 4 to detect presence or absence of body motion during imaging on the basis of the body motion index. In this process, the body motion detector 304 specifies a diffusion-weighted image obtained at the time of occurrence of body motion, as explained for the second embodiment.

In the step S1201 shown in FIG. 12, the body motion-suppressed image generator 801 extracts a diffusion-weighted image obtained in a no body motion period (stationary period) before acquisition of the diffusion-weighted image at the time of occurrence of body motion specified by the body motion detector 304 (refer to FIGS. 6 and 10). The body motion-suppressed image generator 801 generates an image including a characteristic amount such as mean diffusivity (MD) image and diffusion fractional anisotropy (FA) image by using only the extracted diffusion-weighted image obtained in the stationary period for body motion in the step S1202. An image of a diffusion characteristic amount in which influence of body motion is suppressed can be thereby obtained.

Fourth Embodiment

Hereafter, the fourth embodiment of the present invention will be explained. The MRI apparatus of the fourth embodiment further has a function for correcting a diffusion-weighted image obtained in a period where there is body motion as a post treatment after the body motion-suppressed image generator 801 of the third embodiment completes acquisition of a series of diffusion-weighted images 501, in addition to the functions explained for the third embodiment. The configurations of the other parts are the same as those of the third embodiment.

Figure 13:
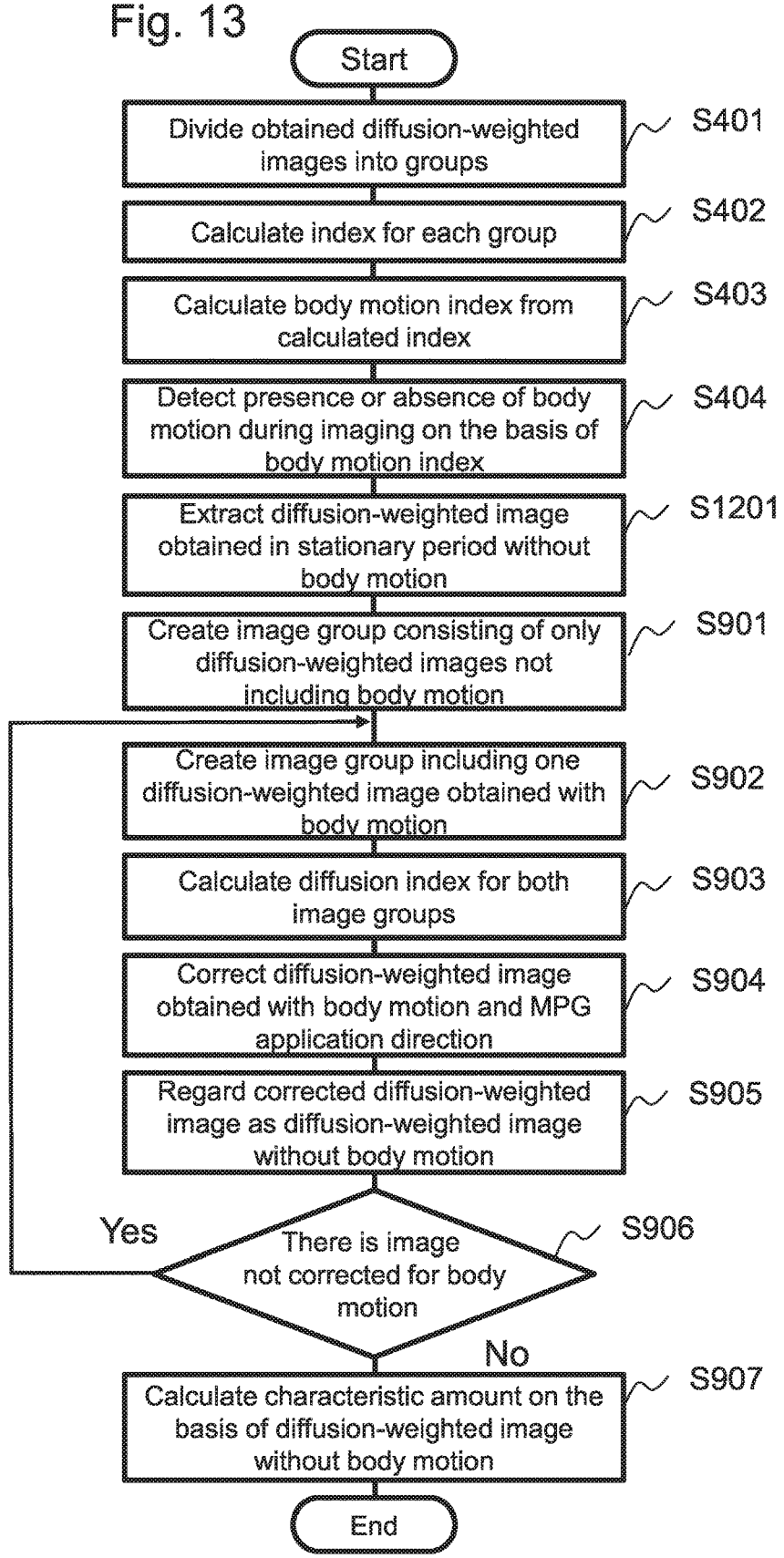
FIG. 13 is a flowchart showing the operation of the image analyzer 110 of the fourth embodiment.

As shown in FIG. 13, the image analyzer 110 of the fourth embodiment performs the steps S401 to S404 and S1201 as shown in FIG. 12 for the third embodiment to detect presence or absence of body motion during imaging on the basis of the body motion index, specifies a diffusion-weighted image obtained at the time of occurrence of body motion, and extracts a diffusion-weighted image obtained in the stationary period without body motion.

Then, the body motion-suppressed image generator 801 makes the group creator 301 create an image group consisting only of diffusion-weighted images obtained in the stationary period without body motion (step S901). Alternatively, the body motion-suppressed image generator 801 may make the group creator 301 choose an image group comprising only diffusion-weighted images obtained in the stationary period without body motion (for example, image group 505 shown in FIG. 6) from a plurality of image groups created in the step S401.

Then, the body motion-suppressed image generator 801 makes the group creator 301 create an image group including only one diffusion-weighted image obtained in a period where body motion occurs (S902). Alternatively, the body motion-suppressed image generator 801 may make the group creator 301 choose an image group including only one diffusion-weighted image obtained in a period where body motion occurs (for example, image group 506 shown in FIG. 6) from a plurality of image groups created in the step S401.

Then, the body motion-suppressed image generator 801 makes the diffusion index calculator 302 calculate a diffusion index image for each of the image groups created or chosen in the steps S901 and S902 (for example, image groups 505 and 506) (S903). Alternatively, the diffusion index images obtained for the image groups in the aforementioned step S402 are read out.

Then, the body motion-suppressed image generator 801 calculates difference of the diffusion index calculated for the image group 505 without body motion obtained in the step S901 and the diffusion index calculated for the image group S901 including a diffusion-weighted image obtained with body motion, and corrects the diffusion-weighted image obtained with body motion included in the image group created in the step S902 so that the difference should be smaller than a threshold defined beforehand.

Figure 14:
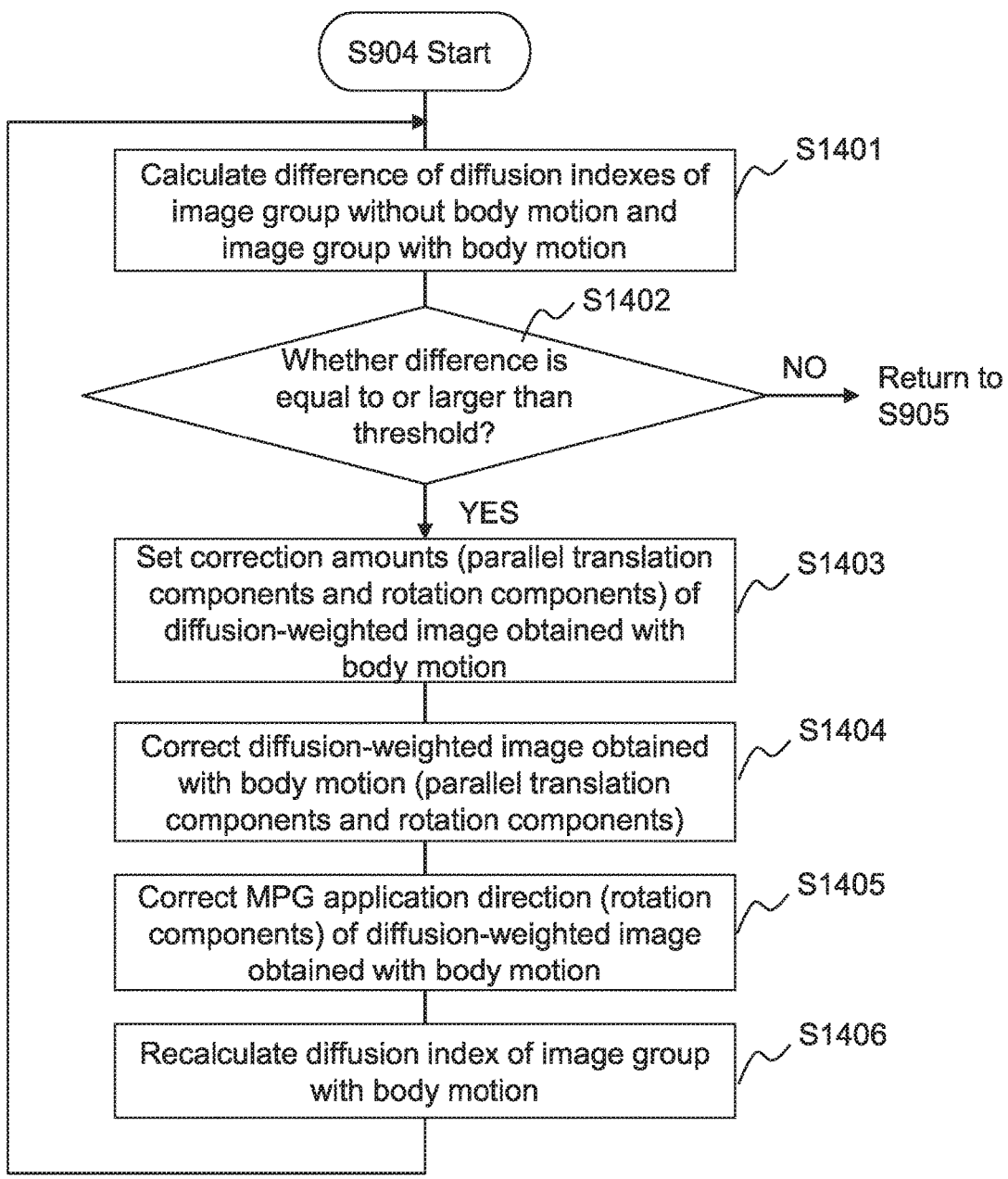
FIG. 14 is a flowchart showing the operation of the image analyzer 110 of the fourth embodiment.

The operation of the step S904 will be explained in more detail with reference to FIG. 14. First, in the step S1401, the body motion-suppressed image generator 801 calculates difference of the diffusion index image MDI calculated for the image group 505 without body motion obtained in the step S903, and the diffusion index image $MD_m$ calculated for the image group 506 including a diffusion-weighted image obtained with body motion in accordance with the following equation (10).

[Equation 10]

$$\min\sum_{i}^{nx}\sum_{j}^{nx}(MD_1(i,j)-MD_m(i,j))^2 \quad nx, ny: \text{number of pixels} \tag{10}$$

Then, when the difference of the diffusion index obtained in the step S1401 is not smaller than the threshold defined beforehand, the process proceeds to the step S1403, and correction amounts defined beforehand for position adjustment and MPG application direction are set. The correction amounts are represented by parallel translation components dx, dy, and dz, and rotation components θx, θy and θz. Ranges and changing step widths of the correction amounts are defined beforehand, and one correction amount in such a range is set for each component.

Then, in the step S1404, the body motion-suppressed image generator 801 corrects the pixel values of the diffusion-weighted image obtained with body motion included in the image group created in the step S902 by parallel translation and rotation according to the parallel translation components dx, dy, and dz, and rotation components θx, θy and θz set in the step S1403.

Further, in the step S1405, the body motion-suppressed image generator 801 corrects the MPG application directions (ex, ey, and ez) of the diffusion-weighted image obtained with body motion included in the image group created in the step S902 using the rotation component θx, θy, and θz obtained in the step S1403 in accordance with the following equation (11) to obtain corrected MPG application directions (ex', ey', ez').

[Equation 11]

$$\begin{pmatrix}ex'\\ey'\\ez'\end{pmatrix} = \begin{pmatrix}ex\\ey\\ez\end{pmatrix}\begin{pmatrix}\cos\theta z & -\sin\theta z & 0\\ \sin\theta z & \cos\theta z & 0\\ 0 & 0 & 1\end{pmatrix}\begin{pmatrix}\cos\theta y & 0 & \sin\theta y\\ 0 & 1 & 0\\ -\sin\theta y & 0 & \cos\theta y\end{pmatrix}\begin{pmatrix}1 & 0 & 0\\ 0 & \cos\theta x & -\sin\theta x\\ 0 & \sin\theta x & \cos\theta x\end{pmatrix} \tag{11}$$

In the step S1406, the body motion-suppressed image generator 801 makes the diffusion index calculator 302 recalculate the diffusion index of the image group created in the step S902 using the pixel values and MPG application directions of the corrected diffusion-weighted image, which has been corrected in the steps S1404 and S1405.

The process returns to the step S1401, and difference of the diffusion index of the image group including the corrected diffusion-weighted image recalculated in the step S1406, and the diffusion index of the image group without body motion specified in the step S1201 is calculated. When the difference is not smaller than the threshold, the steps S1403 to S1406 are repeated with changing the correction amounts by a step width defined beforehand within the range defined beforehand. If the difference is smaller than the threshold, the process proceeds to the step S905.

In the step S905, the diffusion-weighted image of which body motion is corrected in the aforementioned step S904 (steps S1401 to S1406) is recognized as a diffusion-weighted image without body motion. Then, the process proceeds to the step S906, and when there is a diffusion-weighted image obtained with body motion (diffusion-weighted image not obtained in the stationary period without body motion, and in addition, not corrected in the steps S902 to S905), the process returns to the step S902, and the diffusion-weighted image obtained with body motion is corrected.

If all the diffusion-weighted images obtained with body motion are corrected, the process proceeds to the step S907, and characteristic amount of the diffusion-weighted images (for example, MD and FA) is calculated by using the diffusion-weighted image obtained without body motion in the stationary period, and the diffusion-weighted image corrected in the steps S902 to S905.

As explained above, according to this embodiment, body motion included in a diffusion-weighted image can be corrected, and it becomes possible to provide a user with an image of higher quality.

Although such a configuration that all the diffusion-weighted images obtained in the period where there is body motion are corrected in the steps S901 to S906 is employed in the example of this embodiment explained above, the correction amount may be calculated by performing the step S1403 only for the last diffusion-weighted image among the diffusion-weighted images obtained in the period where there is body motion. The current direction of the subject can be thereby recognized. Further, re-imaging is performed for only the diffusion-weighted image obtained in the period where there is body motion with the current direction of the subject. The MPG application directions in the pulse sequence used for the re-imaging in this case are corrected in accordance with the current direction of the subject recognized above. As a result, by using the diffusion-weighted image obtained in the stationary period obtained in the first imaging, and the diffusion-weighted image obtained in the re-imaging performed with the corrected MPG application directions, a series of diffusion-weighted images not including body motion can be obtained.

As described above, according to this embodiment, only the diffusion-weighted image of a period where there is body motion can be obtained again, and therefore time required for the re-imaging can be reduced compared with the case where re-imaging is performed for all the images.

Fifth Embodiment

Figure 15:
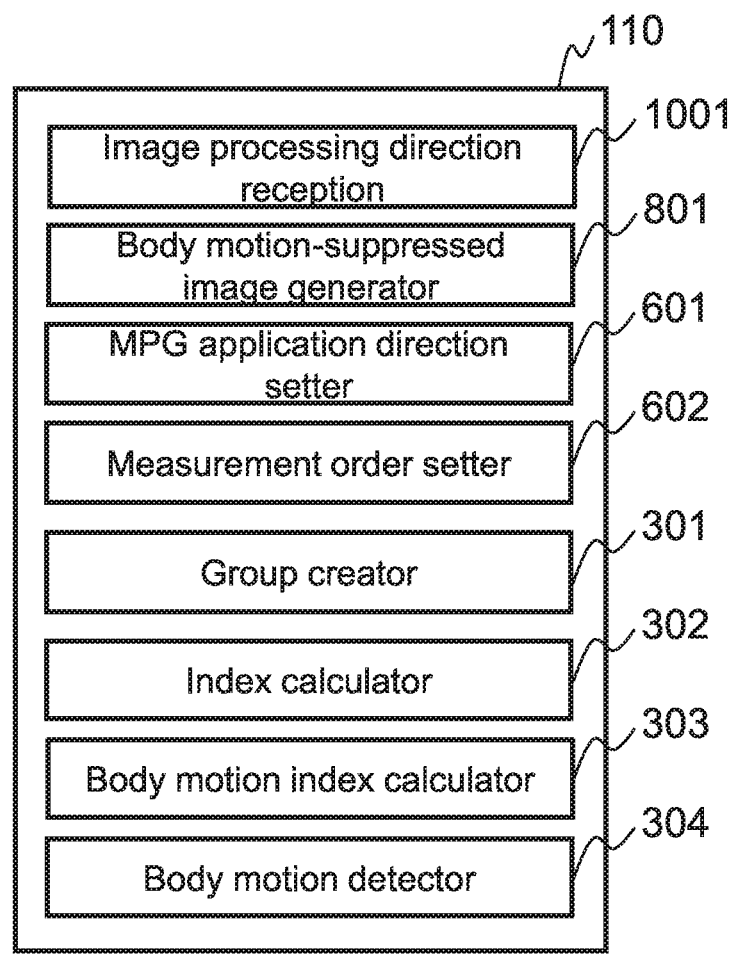
FIG. 15 is a functional block diagram of the image analyzer 110 of the fifth embodiment.

Hereafter, the fifth embodiment of the present invention will be explained. The MRI apparatus of the fifth embodiment further comprises an image processing direction reception 1001 in the image analyzer 110 as shown in FIG. 15. The configurations and functions of the other parts are the same as those of the fourth embodiment.

In the fifth embodiment, the image processing direction reception 1001 receives directions of an operator through a user interface or the like concerning which function should be executed by the body motion-suppressed image generator 801 among the function of calculating a characteristic amount of diffusion image by using only a diffusion-weighted image obtained in a body motion stationary period explained for the third embodiment, the function of calculating a characteristic amount of diffusion image after correcting body motion of a diffusion-weighted image explained for the fourth embodiment, the function of performing re-imaging only for a diffusion-weighted image obtained in a period where there is body motion, and so forth.

Figure 16:
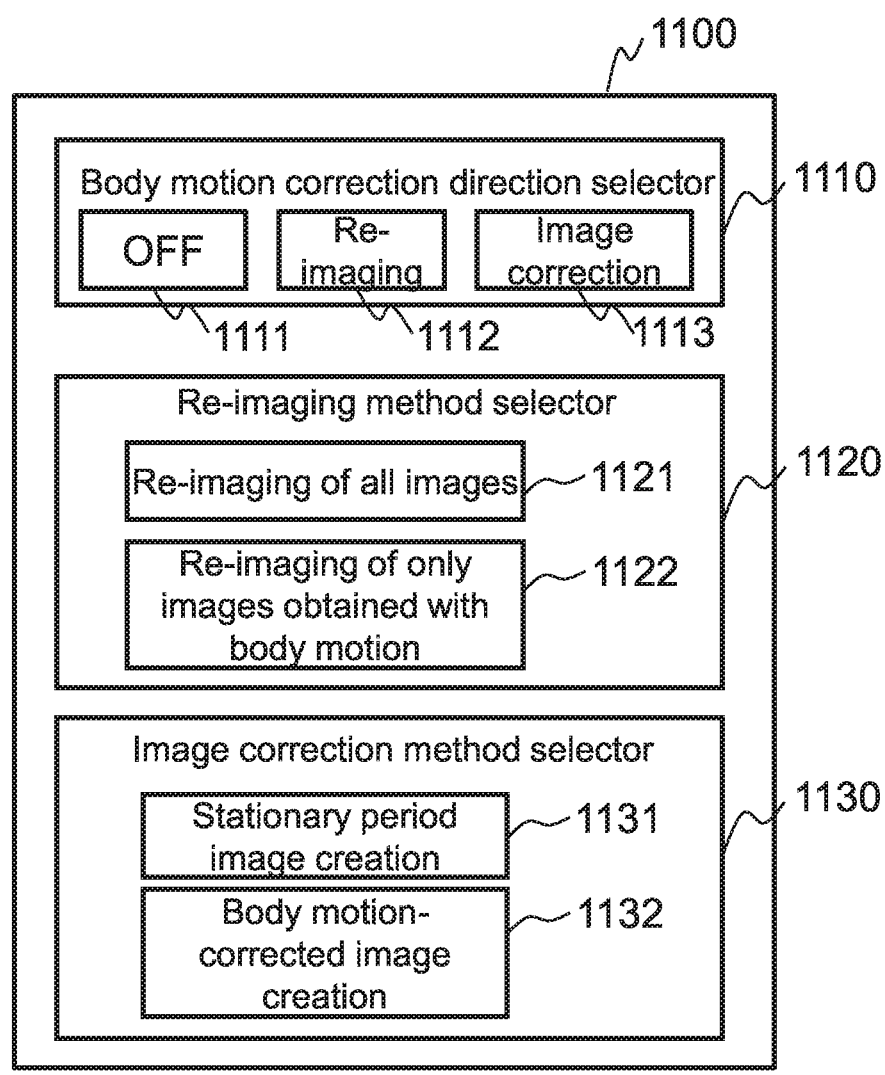
FIG. 16 shows an example of the user interface screen to be displayed on the display according to the fifth embodiment.

An example of the user interface 1100 used in this embodiment is shown in FIG. 16. The user interface 1100 consists of a screen displayed on the display 111 by the image-processing direction reception 1001, and the image-processing direction reception 1001 receives a direction of an operator inputted via an input device 116 on this screen.

As shown in FIG. 16, the user interface 1100 comprises a body motion correction direction selector 1110, a re-imaging method selector 1120, and an image correction method selector 1130.

The body motion correction direction selector 1110 is constituted so that any one of an OFF button 1111 for a direction of not performing body motion correction, a re-imaging button 1112 for a direction of performing re-imaging, or an image correction button 1113 for a direction of not performing re-imaging and correcting an image as a post treatment can be selected.

The re-imaging method selector 1120 is constituted so that, when the re-imaging button 1112 is chosen in the body motion correction direction selector 1110, and the body motion detector 304 determines that where there is body motion, whether re-imaging is performed for all the images (button 1121 for re-imaging of all images), or re-imaging is performed only for an image obtained in a period where there is body motion as in the fourth embodiment (button 1122 for re-imaging of only images obtained with body motion) can be selected.

The image correction method selector 1130 is constituted so that, when the image correction button 1113 is selected in the body motion correction direction selector 1110, and the body motion detector 304 determines that there is body motion, whether an image is formed with only a diffusion-weighted image obtained in a stationary period for body motion as in the third embodiment (stationary period image creation button 1131), or a diffusion-weighted image obtained during body motion is corrected according to the fourth embodiment (body motion-corrected image creation button 1132) can be selected.

The user interface 1100 may be displayed so that an operator can perform such selections as described above when the operator sets the other imaging parameters before imaging, or may be displayed when the body motion detector 304 determines that there is a body motion after imaging, so that it can receive a direction for subsequent operations.

When it is desired to quickly confirm the image, the operator can select the OFF button 1111 in the body motion correction direction selector 1110, and when further prolongation of the imaging time is not desired, but an image of higher quality is desired, the operator can select the image correction button 1113, and the image can be corrected as a post treatment by selecting the stationary period image creation button 1131 or the body motion-corrected image creation button 1132. When it is desired to perform re-imaging in order to obtain an image of higher quality, but it is not desired to prolong the imaging time as far as possible, the button 1122 for re-imaging of only images obtained with body motion can be selected.

As described above, according to the fifth embodiment, the imaging can be performed in accordance with needs of the operator.

EXPLANATION OF NUMERICAL NOTATIONS

100: MRI apparatus
101: Magnet
102: Gradient coil
103: Subject (living body)
104: Sequencer
105: Gradient magnetic field power supply
106: Radio frequency magnetic field generator
107: RF coil
108: RF probe
109: Receiver
110: Image analyzer
120: Computer
111: Display
112: Storage device
113: Shim coil
114: Shim power supply
115: Bed (table)
116: Input device
201, 204: Slice gradient magnetic field
202: RF Pulse
203, 206: MPG pulse
205: RF pulse for refocusing
207, 208: Dephasing gradient magnetic field
209, 212: Frequency encoding
201: Echo
211: Phase encoding
301: Group creator
302: Diffusion index calculator
303: Body motion index calculator
304: Body motion detector
501: Plurality of measured diffusion-weighted images
502: Group created first
503: Group created secondly
514: All created groups
601: MPG application direction setter
602: Measurement order setter
801: Body motion-suppressed image generator
1001: Image processing direction reception
1100: User interface
1110: Body motion correction direction selector
1111: OFF button
1112: Re-imaging button
1113: Image correction button
1120: Re-imaging method selector
1121: Button for re-imaging of all images
1122: Button for re-imaging of only images obtained with body motion
1130: Image correction method selector
1131: Stationary period image creation button
1132: Body motion-corrected image creation button

The invention claimed is:

1. A magnetic resonance imaging apparatus comprising:
a measurement part that acquires a plurality of diffusion-weighted images by applying a diffusion gradient magnetic field pulse in a plurality of different directions defined beforehand according to a predetermined imaging pulse sequence, and
an image analyzer that detects presence or absence of body motion of a subject under imaging using the plurality of the diffusion-weighted images, wherein:
the image analyzer comprises:
a group creator that creates a plurality of image groups each including 6 or more diffusion-weighted images selected from the plurality of the diffusion-weighted images so that the groups differ from one another in one or more of the included diffusion-weighted images,
a diffusion index calculator that calculates value of a predetermined diffusion index that represents a characteristic amount of diffusion-weighted image for each of the image groups from the diffusion-weighted images included in that image group,
a body motion index calculator that calculates value of a predetermined body motion index concerning body motion information from the value of the diffusion index for each of the image groups, and
a body motion detector that determines presence or absence of body motion for each of the image groups on the basis of the value of the body motion index.

2. The magnetic resonance imaging apparatus according to claim 1, wherein:
diffusion directions of the 6 or more diffusion-weighted images that constitute each of the image groups are spatially uniformly distributed.

3. The magnetic resonance imaging apparatus according to claim 1, wherein:
diffusion directions of all the diffusion-weighted images measured by the measurement part are spatially uniformly distributed.

4. The magnetic resonance imaging apparatus according to claim 1, wherein:
the diffusion index includes either one of mean diffusivity and diffusion fractional anisotropy.

5. The magnetic resonance imaging apparatus according to claim 1, wherein:
the body motion index calculator obtains a difference of a value of the diffusion index calculated by the diffusion index calculator for one of the image groups, and a value of the diffusion index calculated for another one of the image groups, and calculates a value of the body motion index from the difference.

6. The magnetic resonance imaging apparatus according to claim 5, wherein:
the body motion detector detects presence or absence of body motion by comparing the value of the body motion index with a threshold determined beforehand.

7. The magnetic resonance imaging apparatus according to claim 1, which further comprises:
a diffusion direction calculator that obtains a plurality of diffusion directions spatially uniformly distributed, and
a measurement order setter that arranges the plurality of the diffusion directions obtained by the diffusion direction calculator in order, repeatedly performs an operation of selecting a predetermined number not smaller than 6 of consecutive diffusion directions with shifting the first diffusion direction of diffusion directions to be selected one by one to create a plurality of sets of diffusion directions, rearranges the diffusion directions so that spatial distribution of the diffusion directions should become uniform in each set, and sets the order of the rearranged diffusion directions in the measurement part as order of diffusion directions for which imaging should be performed, wherein:

the group creator chooses a plurality of diffusion-weighted images corresponding to the plurality of the sets from the plurality of the diffusion-weighted images obtained by the measurement part in the aforementioned imaging order to create the plurality of the image groups.

8. The magnetic resonance imaging apparatus according to claim 1, wherein:

the group creator creates the plurality of the image groups so that the image groups differ from one another in only one diffusion-weighted image included in each of the image groups, and the body motion detector specifies a diffusion-weighted image obtained in a time zone where body motion occurs on the basis of presence or absence of body motion detected for each of the image groups.

9. The magnetic resonance imaging apparatus according to claim 8, which further comprises:

a body motion-suppressed image generator that calculates a predetermined characteristic amount of diffusion-weighted image using only a diffusion-weighted image obtained in a period where there is no body motion before the diffusion-weighted image obtained in a time zone where body motion occurs and specified by the body motion detector is obtained.

10. The magnetic resonance imaging apparatus according to claim 8, wherein:

an amount of body motion included in the diffusion-weighted image obtained in a time zone where body motion occurs and specified by the body motion detector is obtained, and pixels and diffusion directions of the diffusion-weighted image obtained in a time zone where body motion occurs are corrected according to the amount of body motion.

* * * * *